United States Patent [19]

Tsujihara et al.

[11] Patent Number: 5,741,816
[45] Date of Patent: Apr. 21, 1998

[54] HAIR-GROWTH AGENT

[75] Inventors: Kenji Tsujihara; Kunio Saito, both of Saitama-ken; Satoshi Furuuchi, Tokyo-to, all of Japan

[73] Assignee: Tanabe Seiyaku Co., Ltd., Osaka, Japan

[21] Appl. No.: 466,968

[22] Filed: Jun. 6, 1995

[30] Foreign Application Priority Data

Jun. 20, 1994 [JP] Japan ................... 6-136853
Mar. 2, 1995 [JP] Japan ................... 7-042713

[51] Int. Cl.$^6$ ................... A01N 37/02; A01N 37/06
[52] U.S. Cl. ................... 514/547; 514/529; 514/549; 514/552; 514/880; 554/103; 554/105; 554/107
[58] Field of Search ................... 554/107, 105, 554/103; 514/524, 547, 549, 552, 880

[56] References Cited

U.S. PATENT DOCUMENTS

| | | |
|---|---|---|
| 3,949,087 | 4/1976 | Bacq et al. |
| 4,439,438 | 3/1984 | Cavazza |
| 4,713,397 | 12/1987 | Hirama et al. |

FOREIGN PATENT DOCUMENTS

| | | |
|---|---|---|
| 0 129 778 B1 | 1/1985 | European Pat. Off. |
| 0522157 | 1/1993 | European Pat. Off. |
| 0540854 | 5/1993 | European Pat. Off. |
| 0 552 137 A2 | 7/1993 | European Pat. Off. |
| 0 552 138 A2 | 7/1993 | European Pat. Off. |
| 552137 | 7/1993 | European Pat. Off. |
| 552138 | 7/1993 | European Pat. Off. |
| 559625 | 8/1993 | European Pat. Off. |
| 0 559 625 A2 | 9/1993 | European Pat. Off. |
| 0596838 | 5/1994 | European Pat. Off. |
| 0 634 392 A2 | 1/1995 | European Pat. Off. |
| 55-167262 | 12/1980 | Japan |
| 63-41363 | 2/1984 | Japan |
| 63-41364 | 1/1985 | Japan |
| 6-45533 | 8/1986 | Japan |
| 1-199905 | 8/1989 | Japan |
| 5-339218 | 12/1993 | Japan |
| 5-339219 | 12/1993 | Japan |
| 2043443 | 10/1980 | United Kingdom |

OTHER PUBLICATIONS

Nishida et al, chemical abstract of JP-61183206, Aug. 1986.

*Primary Examiner*—Gary Geist
*Assistant Examiner*—Deborah D. Carr
*Attorney, Agent, or Firm*—Browdy and Neimark

[57] ABSTRACT

Disclosed is a hair-growing (restoration) agent which comprises a carnitine compound represented by the formula (I):

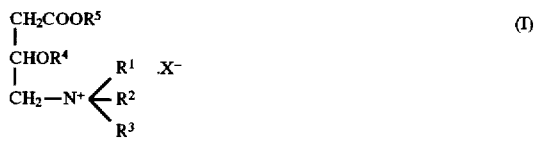

wherein $R^1$ to $R^3$ each represent an alkyl group having 1 to 6 carbon atoms; $R^4$ represents an aliphatic acyl group having 3 to 31 carbon atoms which may be substituted; $R^5$ represents an alkyl group having 3 to 31 carbon atoms which may be substituted, or an alkenyl group having 3 to 31 carbon atoms which may be substituted; and $X^-$ represents an anion of a pharmaceutically acceptable acid, as an active ingredient.

20 Claims, No Drawings

HAIR-GROWTH AGENT

BACKGROUND OF THE INVENTION

This invention relates to a hair-growing (restoration) agent and a carnitine derivative having a hair-growing action.

As energy required for growth of hair, there has generally been used ATP which is generated by metabolism of glucose through glycolysis system and a TCA cycle. However, in male pattern alopecia, phosphofructokinase (PFKase) which is one of enzymes catalyzing glycolysis system is prohibited by male hormones to cause a state that supply of energy is suppressed.

In the prior art, there have been known hair tonics containing pentadecanoic acid monoglyceride and a pelargonic acid ester or a heptadecanoic acid ester of carnitine (3-carboxy-2-hydroxypropyltrimethylammonium hydroxide, intramolecular salt) as an active ingredient (Japanese Patent Publications No. 41363/1988 and No. 45533/1994). Also, there has been known a hair tonic containing a straight aliphatic monovalent alcohol having odd-numbered carbon chain (5 to 25) length as an active ingredient (Japanese Patent Publication No. 41364/1988). Further, in Japanese Provisional Patent Publication No. 199905/1989, it has been described that γ-trialkylammonium-β-hydroxybutyrate chloride (carnitine-hydrochloride) has a hair-nourishing action.

On the other hand, in Japanese Provisional Patent Publication No. 339218/1993, there have been disclosed carnitine derivatives such as undecanoyl-L-carnitine undecyl ester chloride ((R)-2-undecanoyloxy-3-undecyloxycarbonylpropyl)-trimethylammonium chloride). It has been described that these compounds have antibacterial actions, but there is no description regarding a hair-growing action. In Japanese Provisional Patent Publication No. 339219/1993, it has been described that the same compounds as described in Japanese Provisional Patent Publication No. 339218/1993 have antifungal actions, but there is no description regarding a hair-growing action. Further, in Japanese Provisional Patent Publication No. 167262/1980, it has been described that propionylcarnitine isopropyl ester and isobutyrylcarnitine isobutyl ester are useful as an agent for curing myocardial low constriction, but there is no description regarding a hair-growing action.

SUMMARY OF THE INVENTION

An object of the present invention is to provide an excellent hair-growing (restoration) agent containing a carnitine derivative as an active ingredient.

That is, the present invention relates to a hair-growing (restoration) agent which comprises a carnitine derivative represented by the formula (I):

wherein $R^1$ to $R^3$ each represent an alkyl group having 1 to 6 carbon atoms; $R^4$ represents an aliphatic acyl group having 3 to 31 carbon atoms which may be substituted; $R^5$ represents an alkyl group having 3 to 31 carbon atoms which may be substituted, or an alkenyl group having 3 to 31 carbon atoms which may be substituted; and $X^-$ represents an anion of a pharmaceutically acceptable acid, as an active ingredient.

The carnitine derivative (I) of the present invention has an excellent hair-growing action as compared with a conventional hair-growing (restoration) agent and therefore is useful as a hair-growing (restoration) agent.

DESCRIPTION OF THE PREFERRED EMBODIMENTS

In the following, the present invention is explained in detail.

As a specific example of the carnitine derivative (I) which is the active ingredient of the present invention, the alkyl group having 1 to 6 carbon atoms of $R^1$ to $R^3$ includes methyl group, ethyl group, propyl group, butyl group, pentyl group or hexyl group; the aliphatic acyl group having 3 to 31 carbon atoms of $R^4$ includes propionyl group, butyryl group, isobutyryl group, crotonoyl group, methacryloyl group, valeryl group, isovaleryl group, pivaloyl group, hexanoyl group, 4-methylvaleryl group, sorbinoyl group, heptanoyl group, octanoyl group, 2-propylvaleryl group, nonanoyl group, decanoyl group, undecanoyl group, 10-undecenoyl group, dodecanoyl group, tridecanoyl group, tetradecanoyl group, pentadecanoyl group, hexadecanoyl group, heptadecanoyl group, octadecanoyl group, oleoyl group, elaidoyl group, linoleoyl group, linolenoyl group, nonadecanoyl group, 2,6,10,14-tetramethylpentadecanoyl group, icosanoyl group, 3,7,11,15-tetramethylhexadecanoyl group, arachidoyl group, heneicosanoyl group, docosanoyl group, tricosanoyl group, tetracosanoyl group, pentacosanoyl group, hexacosanoyl group, heptacosanoyl group, octacosanoyl group, nonacosanoyl group, triacontanoyl group or hentriacontanoyl group; the alkyl group having 3 to 31 carbon atoms of $R^5$ includes propyl group, isopropyl group, butyl group, isobutyl group, 1-methylpropyl group, 1,1-dimethylethyl group, pentyl group, 1-methylbutyl group, 2-methylbutyl group, 3-methylbutyl group, 1,1-dimethylpropyl group, 1,2-dimethylpropyl group, 2,2-dimethylpropyl group, 1-ethylpropyl group, 2-ethylpropyl group, hexyl group, isohexyl group, 1-methylpentyl group, 2-methylpentyl group, 3-methylpentyl group, 1-ethylbutyl group, 2-ethylbutyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1-ethyl-1-methylpropyl group, 1-ethyl-2-methylpropyl group, 2-ethyl-1-methylpropyl group, 2-ethyl-2-methylpropyl group, 1-methyl-2-ethylpropyl group, 1,1,2-trimethylpropyl group, 1,2,2-trimethylpropyl group, heptyl group, octyl group, 2-propylpentyl group, nonyl group, decyl group, undecyl group, dodecyl group, tridecyl group, tetradecyl group, pentadecyl group, hexadecyl group, heptadecyl group, octadecyl group, nonadecyl group, icosyl group, heneicosyl group, docosyl group, tricosyl group, tetracosyl group, pentacosyl group, hexacosyl group, heptacosyl group, octacosyl group, nonacosyl group, triacontyl group or hentriacontyl group, the alkenyl group having 3 to 31 carbon atoms of $R^5$ includes 2-propenyl group, 1-methyl-ethynyl group, 10-undecenyl group, 14-pentadecenyl group, 3,7,11,15-tetramethyl-2-hexadecenyl group, 20-heneicosenyl group or 30-hentriacontenyl group; and the anion of a pharmaceutically acceptable acid of $X^-$ includes chloride, acetate, citrate, nicotinate, nitrate, sulfonate or salicylate.

The substituent of $R^4$ or $R^5$ includes the alkoxycarbonyl group having 2 to 7 carbon atoms such as methoxycarbonyl group, ethoxycarbonyl group, propyloxycarbonyl group, isopropyloxycarbonyl group, butyloxycarbonyl group, isobutyloxycarbonyl group, pentyloxycarbonyl group, 3-methylbutyloxycarbonyl group, hexyloxycarbonyl group, isohexyloxycarbonyl group, heptyloxycarbonyl group and 5-methyl-hexyloxycarbonyl group.

As a preferred example of the compound (I), there may be mentioned compounds in which each of $R^1$ to $R^3$ is methyl group; $R^4$ is propionyl group, isobutyryl group, valeryl group, hexanoyl group, 4-methylvaleryl group, heptanoyl group, octanoyl group, 2-propylvaleryl group, nonanoyl group, undecanoyl group, 10-undecenoyl group, dodecanoyl group, tridecanoyl group, tetradecanoyl group, pentadecanoyl group, hexadecanoyl group, heptadecanoyl group, linoleoyl group or 3-ethoxycarbonylpropionyl group; and $R^5$ is propyl group, isobutyl group, pentyl group, 1-ethyl-propyl group, 1-methylbutyl group, 2-methylbutyl group, isohexyl group, heptyl group, 2-propylpentyl group, nonyl group, decyl group, undecyl group, dodecyl group, tridecyl group, tetradecyl group, pentadecyl group, heneicosyl group, 10-undecenyl group, 3-ethoxycarbonylpropionyl group or 12-hydroxydodecyl group. Among them, particularly preferred are compounds in which $R^4$ is propionyl group, isobutyryl group, valeryl group, hexanoyl group, 4-methylvaleryl group, heptanoyl group, 2-propylvaleryl group, nonanoyl group, undecanoyl group, 10-undecenoyl group, tridecanoyl group, tetradecanoyl group, pentadecanoyl group, hexadecanoyl group, heptadecanoyl group or linoleoyl group; and $R^5$ is propyl group, pentyl group, 2-methylbutyl group, isohexyl group, heptyl group, nonyl group, decyl group, undecyl group, dodecyl group, tridecyl group, tetradecyl group, pentadecyl group, heneicosyl group or 10-undecenyl group.

As a more preferred example of the compound (I), there may be mentioned compounds in which $R^4$ is propionyl group, isobutyryl group, valeryl group, 4-methylvaleryl group, hexanoyl group, heptanoyl group, undecanoyl group, 10-undecenoyl group, tridecanoyl group or pentadecanoyl group; and $R^5$ is propyl group, pentyl group, 2-methylbutyl group, heptyl group, nonyl group, undecyl group, dodecyl group, tridecyl group, tetradecyl group or pentadecyl group.

Among compounds (I) in which $R^4$ is an unsubstituted aliphatic acyl group having 3 to 31 carbon atoms and $R^5$ is an unsubstituted alkyl group having 3 to 31 carbon atoms or an unsubstituted alkenyl group having 3 to 31 carbon atoms, other preferred compounds are those in which the sum of the carbon number of $R^4$ and the carbon number of $R^5$ is 6 to 34, particularly 14 to 26. As a specific combination of the carbon number of $R^4$ and the carbon number of $R^5$, there may be mentioned, for example, (1) in the case of the sum of the carbon numbers being 6, a combination that the carbon number of $R^4$ is 3 and the carbon number of $R^5$ is 3; (2) in the case of the sum of the carbon numbers being 8, a combination that the carbon number of $R^4$ is 5 and the carbon number of $R^5$ is 3; (3) in the case of the sum of the carbon numbers being 12, a combination that the carbon number of $R^4$ is 5 and the carbon number of $R^5$ is 7; (4) in the case of the sum of the carbon numbers being 14, a combination that the carbon number of $R^4$ is 3 and the carbon number of $R^5$ is 11 or a combination that the carbon number of $R^4$ is 11 and the carbon number of $R^5$ is 3; (5) in the case of the sum of the carbon numbers being 15, a combination that the carbon number of $R^4$ is 4 and the carbon number of $R^5$ is 11; (6) in the case of the sum of the carbon numbers being 16, a combination that the carbon number of $R^4$ is 3 and the carbon number of $R^5$ is 13, a combination that the carbon number of $R^4$ is 5 and the carbon number of $R^5$ is 11, a combination that the carbon number of $R^4$ is 7 and the carbon number of $R^5$ is 9, a combination that the carbon number of $R^4$ is 11 and the carbon number of $R^5$ is 5 or a combination that the carbon number of $R^4$ is 13 and the carbon number of $R^5$ is 3; (7) in the case of the sum of the carbon numbers being 17, a combination that the carbon number of $R^4$ is 4 and the carbon number of $R^5$ is 13, a combination that the carbon number of $R^4$ is 5 and the carbon number of $R^5$ is 12 or a combination that the carbon number of $R^4$ is 6 and the carbon number of $R^5$ is 11; (8) in the case of the sum of the carbon numbers being 18, a combination that the carbon number of $R^4$ is 3 and the carbon number of $R^5$ is 15, a combination that the carbon number of $R^4$ is 4 and the carbon number of $R^5$ is 14, a combination that the carbon number of $R^4$ is 5 and the carbon number of $R^5$ is 13, a combination that the carbon number of $R^4$ is 6 and the carbon number of $R^5$ is 12, a combination that the carbon number of $R^4$ is 7 and the carbon number of $R^5$ is 11, a combination that the carbon number of $R^4$ is 9 and the carbon number of $R^5$ is 9, a combination that the carbon number of $R^4$ is 11 and the carbon number of $R^5$ is 7, a combination that the carbon number of $R^4$ is 13 and the carbon number of $R^5$ is 5 or a combination that the carbon number of $R^4$ is 15 and the carbon number of $R^5$ is 3; (9) in the case of the sum of the carbon numbers being 19, a combination that the carbon number of $R^4$ is 4 and the carbon number of $R^5$ is 15, a combination that the carbon number of $R^4$ is 6 and the carbon number of $R^5$ is 13, a combination that the carbon number of $R^4$ is 8 and the carbon number of $R^5$ is 11, a combination that the carbon number of $R^4$ is 11 and the carbon number of $R^5$ is 8, a combination that the carbon number of $R^4$ is 13 and the carbon number of $R^5$ is 6, a combination that the carbon number of $R^4$ is 15 and the carbon number of $R^5$ is 4 or a combination that the carbon number of $R^4$ is 16 and the carbon number of $R^5$ is 3; (10) in the case of the sum of the carbon numbers being 20, a combination that the carbon number of $R^4$ is 5 and the carbon number of $R^5$ is 15, a combination that the carbon number of $R^4$ is 7 and the carbon number of $R^5$ is 13, a combination that the carbon number of $R^4$ is 9 and the carbon number of $R^5$ is 11, a combination that the carbon number of $R^4$ is 11 and the carbon number of $R^5$ is 9 or a combination that the carbon number of $R^4$ is 13 and the carbon number of $R^5$ is 7; (11) in the case of the sum of the carbon numbers being 21, a combination that the carbon number of $R^4$ is 8 and the carbon number of $R^5$ is 13, a combination that the carbon number of $R^4$ is 16 and the carbon number of $R^5$ is 5 or a combination that the carbon number of $R^4$ is 18 and the carbon number of $R^5$ is 3; (12) in the case of the sum of the carbon numbers being 22, a combination that the carbon number of $R^4$ is 11 and the carbon number of $R^5$ is 11, a combination that the carbon number of $R^4$ is 7 and the carbon number of $R^5$ is 15 or a combination that the carbon number of $R^4$ is 13 and the carbon number of $R^5$ is 9; (13) in the case of the sum of the carbon numbers being 23, a combination that the carbon number of $R^4$ is 8 and the carbon number of $R^5$ is 15; (14) in the case of the sum of the carbon numbers being 25, a combination that the carbon number of $R^4$ is 13 and the carbon number of $R^5$ is 12, a combination that the carbon number of $R^4$ is 14 and the carbon number of $R^5$ is 11 or a combination that the carbon number of $R^4$ is 16 and the carbon number of $R^5$ is 9; (15) in the case of the sum of the carbon numbers being 26, a combination that the carbon number of $R^4$ is 13 and the carbon number of $R^5$ is 13 or a combination that the carbon number of $R^4$ is 15 and the carbon number of $R^5$ is 11; (16) in the case of the sum of the carbon numbers being 27, a combination that the carbon number of $R^4$ is 16 and the carbon number of $R^5$ is 11; (17) in the case of the sum of the carbon numbers being 28, a combination that the carbon number of $R^4$ is 15 and the carbon number of $R^5$ is 13, a combination that the carbon number of $R^4$ is 17 and the carbon number of $R^5$ is 11 or a combination that the carbon number of $R^4$ is 16 and the carbon number of $R^5$ is 12; (18) in the case of the sum of the carbon numbers being 30, a combination that the carbon number of $R^4$ is 15 and the carbon number of $R^5$ is 15; and (19) in the case of the sum of the carbon numbers being 34 a combination that the carbon number of $R^4$ is 13 and the carbon number of $R^5$ is 21, respectively. These unsubstituted $R^4$ and $R^5$ may be substituted.

Other preferable compounds are those in which each of $R^1$ to $R^3$ is an alkyl group having 1 to 6 carbon atoms, $R^4$ is an aliphatic acyl group having 4 to 31 carbon atoms, $R^5$ is an alkyl group having 11 to 31 carbon atoms. Other preferable compounds are those in which the aliphatic acyl group of $R^4$ or the alkyl group of $R^5$ is a branched aliphatic acyl group having 4 to 15 carbon atoms or a branched alkyl group having 4 to 15 carbon atoms. As to a preferable branched aliphatic acyl group or a preferable branched alkyl group, there may be mentioned an aliphatic group or an alkyl group which have a branched methyl group. Moreover, those in which the methyl group branches off from a even-numbered position of carbon chain are more preferable. Furthermore, those in which the even-numbered position of carbon chain is the position neighboring the terminal carbon atom are most preferable.

In the carnitine derivative (I) which is the active ingredient of the present invention, as the aliphatic acyl group of $R^4$, there may be mentioned those in which whose carbon numbers are even or odd, those which are straight or branched, or those which are saturated or unsaturated, respectively. As the alkyl group or the alkenyl group of $R^5$, there may be mentioned those in which whose carbon numbers are even or odd, those which are straight or branched, respectively.

The carnitine derivative (I) according to the present invention includes optical isomers based on an asymmetric carbon atom at 2-position of carnitine (3-carboxy-2-hydroxypropyltrimethylammonium hydroxide, intramolecular salt) and an asymmetric carbon atom existing at $R^1$, $R^2$, $R^3$, $R^4$ or $R^5$, and mixtures thereof. Among them, a compound in which asymmetric carbon atom at 2-position of carnitine is R configuration is particularly preferred from the point of a pharmaceutical effect.

In the present invention, a preferred carnitine compound (I) may include those in which (1) each of $R^1$ to $R^3$ is methyl group; $R^4$ is pentadecanoyl group and $R^5$ is undecyl group;

(2) each of $R^1$ to $R^3$ is methyl group; $R^4$ is 4-methylvaleryl group and $R^5$ is undecyl group;

(3) each of $R^1$ to $R^3$ is methyl group; $R^4$ is valeryl group and $R^5$ is tridecyl group;

(4) each of $R^1$ to $R^3$ is methyl group; $R^4$ is propionyl group and $R^5$ is undecyl group;

(5) each of $R^1$ to $R^3$ is methyl group; $R^4$ is tridecanoyl group and $R^5$ is pentyl group;

(6) each of $R^1$ to $R^3$ is methyl group; $R^4$ is heptanoyl group and $R^5$ is nonyl group;

(7) each of $R^1$ to $R^3$ is methyl group; $R^4$ is heptanoyl group and $R^5$ is tridecyl group;

(8) each of $R^1$ to $R^3$ is methyl group; $R^4$ is undecanoyl group and $R^5$ is pentyl group;

(9) each of $R^1$ to $R^3$ is methyl group; $R^4$ is valeryl group and $R^5$ is undecyl group;

(10) each of $R^1$ to $R^3$ is methyl group; $R^4$ is undecanoyl group and $R^5$ is heptyl group;

(11) each of $R^1$ to $R^3$ is methyl group; $R^4$ is tridecanoyl group and $R^5$ is heptyl group;

(12) each of $R^1$ to $R^3$ is methyl group; $R^4$ is isobutyryl group and $R^5$ is tridecyl group;

(13) each of $R^1$ to $R^3$ is methyl group; $R^4$ is propionyl group and $R^5$ is tridecyl group;

(14) each of $R^1$ to $R^3$ is methyl group; $R^4$ is 4-methylvaleryl group and $R^5$ is dodecyl group;

(15) each of $R^1$ to $R^3$ is methyl group; $R^4$ is 4-methylvaleryl group and $R^5$ is tridecyl group;

(16) each of $R^1$ to $R^3$ is methyl group; $R^4$ is isobutyryl group and $R^5$ is tetradecyl group;

(17) each of $R^1$ to $R^3$ is methyl group; $R^4$ is valeryl group and $R^5$ is pentadecyl group;

(18) each of $R^1$ to $R^3$ is methyl group; $R^4$ is propionyl group and $R^5$ is pentadecyl group; and

(19) each of $R^1$ to $R^3$ is methyl group; $R^4$ is hexanoyl group and $R^5$ is undecyl group.

The hair-growing (restoration) agent of the present invention can be applied in various forms such as a hair tonic, a hair lotion, hair cream, shampoo and a conditioner according to a conventional method. In addition to the carnitine derivative which is the active ingredient of the present invention, materials which are generally used for these hair-growing (restoration) agents may be formulated into these hair-growing (restoration) agents. For example, distilled water, alcohols, polyvalent alcohols, a surfactant and fats and oils may be formulated as a base material, and further there can be formulated simultaneously materials which have been formulated in known hair-growing (restoration) agents, such as vitamins, hormones, a vasodilator, amino acids, an antiphlogistic, a skin function-accelerating agent and a cuticle-dissolving agent.

The amount of the active ingredient of the present invention to be formulated is not particularly limited, and the active ingredient may be formulated in a suitable amount depending on the amounts and kinds of other formulated materials such as a base material. In general, the amount is suitably about 0.1 to 2% by weight based on the total amount formulated.

The carnitine derivative (I) of the present invention can be prepared by, for example, condensing a compound represented by the formula (II):

(II)

wherein $R^1$, $R^2$, $R^3$ and $R^4$ have the same meanings as described above, and a compound represented by the formula (III):

(III)

wherein Y represents a halogen atom; and $R^5$ has the same meaning as described above.

Also, the carnitine derivative (I) of the present invention can be prepared by, for example, condensing a compound represented by the formula (II):

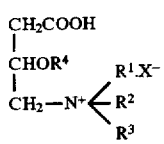

(II)

wherein $R^1$, $R^2$, $R^3$ and $R^4$ have the same meanings as described above,
or a reactive derivative thereof having reactivity at carboxyl group and a compound represented by the formula (IV):

R⁵OH                                            (IV)

wherein $R^5$ has the same meaning as described above.

The condensation of the compound (II) and the compound (III) and the condensation of the reactive derivative of the compound (II) and the compound (IV) can be suitably carried out in a suitable solvent (e.g., dimethylformamide, tetrahydrofuran, methylene chloride, ethyl acetate and acetonitrile) in the presence or absence of an acid acceptor (e.g., an alkali metal hydroxide, an alkali metal carbonate, an alkali metal hydrogen carbonate, N,N-dialkylaniline, pyridine, N-alkylmorpholine and a tri-lower alkylamine) at 0° to 60° C.

The condensation of the compound (II) and the compound (IV) can be carried out suitably in the same solvent as described in the above condensations in the presence or absence of a condensing agent (e.g., N,N'-dicyclohexylcarbodiimide, N-cyclohexyl-N'-morpholinocarbodiimide and N-ethyl-N'-(3-dimethylaminopropyl)carbodiimide) at –30° to 30° C.

As the reactive derivative of the compound (II), there may be used a corresponding acid halide, mixed acid anhydride or active ester.

If desired, the carnitine derivative (I) of the present invention thus obtained may be reacted with, for example, an alkali metal salt (e.g., sodium salt and potassium salt) of a pharmaceutically acceptable acid to convert $X^-$ into an anion of other pharmaceutically acceptable acid.

The starting compound (II) can be prepared by reacting a carnitine derivative represented by the formula (V):

(V)

wherein $R^1$, $R^2$ and $R^3$ have the same meanings as described above,
with a carboxylic acid compound represented by the formula (VI):

R⁴OH                                            (VI)

wherein $R^4$ has the same meaning as described above, according to a conventional method, for example, in the same manner as in the above condensation.

In the present specification, as a preferable example of an alkyl group having 1 to 6 carbon atoms, there may be mentioned an alkyl group having 1 to 4 carbon atoms, particularly methyl group; as a preferable example of an alkyl group having 3 to 31 carbon atoms, there may be mentioned an alkyl group having 3 to 21 carbon atoms, particularly an alkyl group having 3 to 15 carbon atoms; as a preferable example of an alkenyl group having 3 to 31 carbon atoms, there may be mentioned an alkenyl group having 3 to 21 carbon atoms, particularly an alkenyl group having 3 to 15 carbon atoms; as a preferable example of an aliphatic acyl group having 3 to 31 carbon atoms, there may be mentioned an aliphatic acyl group having 3 to 18 carbon atoms, particularly an aliphatic acyl group having 3 to 15 carbon atoms; and as a preferable example of an alkoxy group, there may be mentioned an alkoxy group having 1 to 4 carbon atoms.

Further, in the present specification, as the anion of the pharmaceutically acceptable acid, there may be mentioned, for example, chloride, acetate, citrate, nicotinate, nitrate, sulfonate and salicylate. Among them, chloride, nicotinate, nitrate and sulfonate are preferred, and chloride, nicotinate and nitrate are particularly preferred.

EXAMPLES

The present invention is described in detail by referring to Examples.

Test example 1 (Hair-growing action on shaved mouse)
Method

Backs of 10 male C3H/HeN mice (6 weeks old) per group were shaved by an electric hair clipper and then a safety razor 3 days before application of samples was initiated. 0.1 ml of an ethanol solution containing 2% (w/v) or 0.5% (w/v) of each sample or ethanol (control group) was applied to a shaved portion once a day for 30 days at 5 successive days a week after the mice became 7 weeks old.

The hair-growing action was evaluated by scoring hair-growing degrees based on the following 6 ranks.

0: No growth of hair is observed.

1: Hard hair is grown at less than 25% of a shaved portion.

2: Hard hair is grown at 25% to less than 50% of a shaved portion.

3: Hard hair is grown at 50% to less than 75% of a shaved portion.

4: Hard hair is grown at 75% to less than 100% of a shaved portion.

5: Hard hair is grown at 100% of a shaved portion.
Results

The results are shown in the following Table 1 (using 2% solution of each sample) and Table 2 (using 0.5% solution of each sample), respectively.

TABLE 1

| Example No.*¹ | Hair-growing score (average value, after 30 days) |
|---|---|
| Control | 2.0*² |
| 1 | 4.6 |
| 3 | 4.6 |
| 8 | 4.1 |
| 9 | 5.0 |
| 11 | 5.0 |
| 12 | 5.0 |
| 13 | 3.4 |
| 14 | 5.0 |
| 19 | 3.7 |
| 22 | 5.0 |
| 24 | 4.9 |
| 25 | 5.0 |
| 30 | 5.0 |
| 35 | 5.0 |
| 39 | 3.9 |
| 41 | 4.9 |
| 42 | 4.4 |
| 43 | 5.0 |
| 44 | 5.0 |
| 46 | 5.0 |

TABLE 1-continued

| Example No.*[1] | Hair-growing score (average value, after 30 days) |
| --- | --- |
| 47 | 4.9 |
| 48 | 4.4 |
| 49 | 4.1 |
| 51 | 5.0 |
| 53 | 5.0 |
| 54 | 4.8 |
| 55 | 4.4 |
| 56 | 4.2 |
| 58 | 4.2 |
| 62 | 3.9 |
| 63 | 4.3 |
| 64 | 4.0 |

*[1] showing a sample prepared in the respective Examples described below
*[2] the average value obtained by carrying out the above test 5 times in the case of Control

TABLE 2

| Example No.*[1] | Hair-growing score (average value, after 30 days) |
| --- | --- |
| Control | 2.0*[2] |
| 15 | 4.0 |
| 16 | 4.3 |
| 17 | 4.4 |
| 18 | 5.0 |
| 23 | 4.8 |
| 26 | 4.7 |
| 27 | 4.6 |
| 28 | 4.9 |
| 29 | 5.0 |
| 31 | 3.8 |
| 32 | 4.6 |
| 33 | 4.5 |
| 36 | 4.7 |
| 37 | 4.3 |
| 38 | 5.0 |
| 52 | 3.6 |
| 65 | 4.6 |
| 66 | 3.9 |
| 67 | 3.8 |
| 70 | 3.5 |
| 74 | 4.4 |
| 76 | 3.8 |
| 77 | 3.8 |
| 80 | 4.0 |

*[1] showing a sample prepared in the respective Examples described below
*[2] the average value obtained by carrying out the above test 5 times in the case of Control

EXAMPLE 1

Triethylamine (0.53 ml, 3.81 mmol) and 1-bromotridecane (5.0 g, 19.0 mmol) were added successively to a suspension of (R)-(3-carboxy-2-tridecanoyloxypropyl)trimethylammonium chloride (1.5 g, 3.81 mmol) in 30 ml of dimethylformamide, and the mixture was stirred for 23 hours at 50° to 60° C. under argon atmosphere. The solvent of the reaction mixture was removed under reduced pressure. To the residue was added 20 ml of diethyl ether, and the mixture was stirred at room temperature. Thereafter, the precipitates were collected by filtration, washed with diethyl ether, and dried to give 2.5 g of crude (R)-(2-tridecanoyloxy-3-tridecyloxycarbonylpropyl)trimethylammonium bromide as a colorless solid. To 2.5 g of the product thus obtained was added 50 ml of water, and the mixture was stirred for 1 hour at room temperature and then extracted with tetrahydrofuran-ethyl acetate (1:1). To the extracted organic layer were added 100 ml of a saturated saline solution and 30 ml of water, and the mixture was stirred for 18 hours at room temperature. Thereafter, the organic layer was collected, washed with a saturated saline solution and then water, and the solvent was removed under reduced pressure. The residue was azeotroped with ethyl acetate and then dried at room temperature under reduced pressure to afford 1.75 g of a crude desired product. The product obtained was recrystallized from ethyl acetate to provide 1.58 g of (R)-(2-tridecanoyloxy-3-tridecyloxycarbonylpropyl)trimethylammonium chloride as colorless crystals.

m.p.: 146° to 147° C.

IR (Nujol) cm$^{-1}$: 1735, 1725

NMR (CDCl$_3$) δ: 0.88 (6H, t, J=6.8Hz), 1.26 (38H, br s), 1.55 to 1.65 (4H, m), 2.31 to 2.36 (2H, m), 2.80 (1H, dd, J=17, 5.9Hz), 2.85 (1H, dd, J=17, 6.8Hz), 3.52 (9H, s), 4.01 to 4.13 (3H, m), 4.32 (1H, br d), 5.64 to 5.71 (1H, m)

EXAMPLE 2

By processing (R)-(3-carboxy-2-pentadecanoyloxypropyl)trimethylammonium chloride in the same manner as described in Example 1, (R)-(2-pentadecanoyloxy-3-tridecyloxycarbonylpropyl)trimethylammonium chloride was obtained.

m.p.: 153° to 154° C.

IR (Nujol) cm$^{-1}$: 1760, 1740, 1730

NMR (CDCl$_3$) δ: 0.88 (6H, t, J=6.8Hz), 1.26 (42H, br s), 1.55 to 1.65 (4H, m), 2.30 to 2.36 (2H, m), 2.80 (1H, dd, J=17, 6.0Hz), 2.85 (1H, dd, J=17, 6.8Hz), 3.53 (9H, s), 4.03 to 4.12 (3H, m), 4.34 (br d), 5.64 to 5.71 (1H, m)

EXAMPLE 3

Under ice cooling, oxalyl chloride (1.41 g, 11.1 mmol) was added dropwise to a suspension of (R)-(3-carboxy-2-pentadecanoyloxypropyl)trimethylammonium chloride (2 g, 4.74 mmol) in 10 ml of methylene chloride, and the mixture was then stirred for 2.5 hours at room temperature. After the solvent of the mixture was removed under reduced pressure, the residue was azeotroped with toluene (15 ml×2) to give crude acid chloride as a colorless solid. To a solution of the acid chloride in 10 ml of methylene chloride was added dropwise 1-undecanol (1.49 ml, 7.2 mmol) under argon atmosphere while ice cooling. After the reaction mixture was stirred for 2.5 hours under ice cooling and then stirred for 30 minutes at room temperature, and the solvent was removed. To the residue was added 60 ml of diethyl ether, and the mixture was stirred for 15 minutes at room temperature. The precipitates were collected by filtration, washed with diethyl ether and then dried to give 2.62 g of a crude desired product as a colorless solid. To 2.62 g of the product obtained was added 50 ml of water, and the mixture was stirred for 1 hour at room temperature and then extracted with tetrahydrofuran-ethyl acetate (1:1). The solvent of the extracts was removed under reduced pressure, and the residue was azeotroped with ethyl acetate. Thereafter, the residual solid was recrystallized from acetonitrile to afford 2.0 g of (R)-(2-pentadecanoyloxy-3-undecyloxycarbonylpropyl)trimethylammonium chloride as colorless crystals.

m.p.: 152° to 153° C.

IR (Nujol) cm$^{-1}$: 1760, 1740, 1730

NMR (CDCl$_3$) δ: 0.88 (6H, t, J=6.7Hz), 1.26 (38H, br s), 1.54 to 1.66 (4H, m), 2.30 to 2.36 (2H, m), 2.80 (1H, dd, J=17, 5.9Hz), 2.85 (1H, dd, J=17, 6.7Hz), 3.53 (9H, s), 4.03 to 4.11 (3H, m), 4.34 (br d), 5.64 to 5.71 (1H, m)

EXAMPLES 4 and 5

By processing corresponding starting compounds in the same manner as described in Example 3, the compounds shown in the following Table 3 were obtained.

TABLE 3

$$\begin{array}{c} CH_2COOR^5 \\ | \\ CHOR^4 \\ | \\ CH_2-N^+ \begin{array}{c} CH_3 \\ -CH_3 \\ CH_3 \end{array} \quad X^- \end{array}$$

| Example No. | $R^4$ | $R^5$ | $X^-$ | Physical properties |
|---|---|---|---|---|
| 4 | $-CO(CH_2)_{13}CH_3$ | $-(CH_2)_{14}CH_3$ | $Cl^-$ | m.p.: 156 to 157° C. IR(Nujol)cm$^{-1}$: 1740, 1730 NMR(DMSO-d$_6$)δ: 0.85 (6H, t, J=6.7Hz), 1.24(46H, br s), 1.45 to 1.60(4H, m), 2.22 to 2.40(2H, m), 2.73(1H, dd, J=16, 5.7Hz), 2.79(1H, dd, J=16, 6.0Hz), 3.10 (9H, s), 3.67(1H, br d), 3.80(1H, dd, J=14, 8.4Hz), 4.02 (2H, t, J=6.4Hz), 5.46 to 5.53(1H, m) |
| 5 | $-CO(CH_2)_{15}CH_3$ | $-(CH_2)_{10}CH_3$ | $Cl^-$ | m.p.: 148 to 149° C. IR(Nujol)cm$^{-1}$: 1760, 1740, 1730 NMR(CDCl$_3$)δ: 0.88 (6H, t, J=6.7Hz), 1.26(42H, br s), 1.55 to 1.65(4H, m), 2.30 to 2.36(2H, m), 2.80(1H, dd, J=17, 6.1Hz), 2.85(1H, dd, J=17, 6.6Hz), 3.53 (9H, s), 4.01 to 4.13 (3H, m), 4.34(1H, br d), 5.64 to 5.71(1H, m) |

EXAMPLE 6

To a suspension of (R)-(2-pentadecanoyloxy-3-tridecyloxycarbonylpropyl)trimethylammonium chloride (1.5 g, 2.48 mmol) obtained in Example 2 and sodium nicotinate (3.0 g, 20.7 mmol) in 30 ml of tetrahydrofuran-ethyl acetate (1:1) was added 15 ml of water, and the mixture was stirred for 46.5 hours at room temperature. After the organic layer was separated and washed with 10 ml of water, the solvent was removed under reduced pressure, and the residue was azeotroped with ethyl acetate. The residual oily product was dissolved in 20 ml of diethyl ether, and the insoluble materials were removed by filtration. After diethyl ether was removed under reduced pressure, the residue was dried to give 1.62 g of (R)-(2-pentadecanoyloxy-3-tridecyloxycarbonylpropyl)trimethylammonium nicotinate as a colorless solid.

m.p.: 62° to 68° C.

IR (Nujol) cm$^{-1}$: 1740, 1610

NMR (CDCl$_3$) δ: 0.88 (6H, t, J=6.7Hz), 1.26 (42H, br s), 1.56 to 1.63 (4H, m), 2.25 to 2.31 (2H, m), 2.77 (1H, dd, J=17, 5.7Hz), 2.82 (1H, dd, J=17, 6.9Hz), 3.49 (9H, s), 3.97 to 4.18 (3H, m), 4.35 (1H, br d), 5.63 to 5.71 (1H, m), 7.25 (1H, dd, J=7.7, 4.8Hz), 8.30 (1H, dt, J=7.7, 1.8Hz), 8.56 (1H, m), 9.23 (1H, br s)

EXAMPLES 7 to 11

By processing corresponding starting compounds in the same manner as described in Example 1 or 3, the compounds shown in the following Table 4 were obtained.

TABLE 4

$$\begin{array}{c} CH_2COOR^5 \\ | \\ CHOR^4 \\ | \\ CH_2-N^+{\Large\langle}\begin{array}{c}CH_3\\CH_3\\CH_3\end{array} \quad X^- \end{array}$$

| Example No. | R⁴ | R⁵ | X⁻ | Physical properties |
|---|---|---|---|---|
| 7 | —CO(CH₂)₁₄CH₃ | —(CH₂)₁₀CH₃ | Cl⁻ | m.p.: 158 to 159° C. IR(Nujol)cm⁻¹: 1760, 1740, 1730 NMR(CDCl₃)δ: 0.88 (6H, t, J=6.7Hz), 1.26(40H, br s), 1.54 to 1.65(4H, m), 2.30 to 2.36(2H, m), 2.80(1H, dd, J=17, 5.9Hz), 2.85(1H, dd, J=17, 6.6Hz), 3.53 (9H, s), 4.03 to 4.11 (3H, m), 4.34(1H, br d), 5.64 to 5.71(1H, m) |
| 8 | —CO(CH₂)₉CH₃ | —(CH₂)₁₀CH₃ | Cl⁻ | m.p.: 135 to 136° C. IR(Nujol)cm⁻¹: 1730, 1720 NMR(CDCl₃)δ: 0.88 (6H, t, J=6.7Hz), 1.26(30H, br s), 1.54 to 1.65(4H, m), 2.31 to 2.36(2H, m), 2.80(1H, dd, J=17, 5.8Hz), 2.86(1H, dd, J=17, 6.7Hz), 3.52 (9H, s), 4.01 to 4.13 (3H, m), 4.32(br d), 5.64 to 5.71(1H, m) |
| 9 | —CO(CH₂)₁₁CH₃ | —(CH₂)₁₁CH₃ | Cl⁻ | m.p.: 145 to 147° C. IR(Nujol)cm⁻¹: 1730, 1720 NMR(CDCl₃)δ: 0.88 (6H, t, J=6.7Hz), 1.26 (36H, br s), 1.54 to 1.65(4H, m), 2.30 to 2.36(2H, m), 2.80 (1H, dd, J=17, 6.0Hz), 2.85(1H, dd, J=17, 6.7Hz), 3.52(9H, s), 4.01 to 4.13(3H, m), 4.32(1H, br d), 5.64 to 5.71(1H, m) |
| 10 | —CO(CH₂)₁₄CH₃ | —(CH₂)₁₁CH₃ | Cl⁻ | m.p.: 153 to 154° C. IR(Nujol)cm⁻¹: 1750, 1740, 1730 NMR(CDCl₃)δ: 0.88 (6H, t, J=6.7Hz), 1.26(42H, br s), 1.54 to 1.65(4H, m), 2.31 to 2.36(2H, m), 2.80(1H, dd, J=17, 5.8Hz), 2.86(1H, dd, J=17, 6.7Hz), 3.49 (9H, s), 4.01 to 4.11 (3H, m), 4.28(1H, br d), 5.64 to 5.71(1H, m) |

TABLE 4-continued

$$\begin{array}{c} CH_2COOR^5 \\ | \\ CHOR^4 \\ | \\ CH_2-N^+\!\!\!<\!\!\!\begin{array}{c}CH_3\\CH_3\\CH_3\end{array} \quad X^- \end{array}$$

| Example No. | $R^4$ | $R^5$ | $X^-$ | Physical properties |
|---|---|---|---|---|
| 11 | $-CO(CH_2)_5CH_3$ | $-(CH_2)_{12}CH_3$ | $Cl^-$ | m.p.: 55 to 65°C. IR(Neat)cm$^{-1}$: 2920, 2840, 1740 NMR(CDCl$_3$)δ: 0.85 to 0.90(6H, m), 1.26(26H, m), 1.55 to 1.65(4H, m), 2.34(2H, t, J=7.7 Hz), 2.80 to 2.90(2H, m), 3.51(9H, s), 4.00 to 4.10(3H, m), 4.33 (1H, d, J=14Hz), 5.60 to 5.70(1H, m) |

EXAMPLE 12

By processing (R)-(2-tridecanoyloxy-3-tridecyloxycarbonylpropyl)trimethylammonium chloride obtained in Example 1 in the same manner as described in Example 6, (R)-(2-tridecanoyloxy-3-tridecyloxycarbonylpropyl)trimethylammonium nicotinate was obtained as an oily product.

IR (Neat) cm$^{-1}$: 2920, 2840, 1740

NMR (CDCl$_3$) δ: 0.88 (6H, t, J=7.0Hz), 1.26 (38H, s), 1.55 to 1.65 (4H, m), 2.28 (2H, t, J=7.3Hz), 2.76 (1H, dd, J=5.5, 17Hz), 2.85 (1H, dd, J=7.3, 17Hz), 3.46 (9H, s), 4.00 to 4.20 (3H, m), 4.34 (1H, d, J=14Hz), 5.65 to 5.68 (1H, m), 7.20 to 7.25 (1H, m), 8.31 (1H, dt, J=7.8, 1.9Hz), 8.56 (1H, dd, J=1.1, 4.6Hz), 9.22 (1H, s)

EXAMPLES 13 and 14

By processing corresponding starting compounds in the same manner as described in Example 1 or 3, the compounds shown in the following Table 5 were obtained.

TABLE 5

$$\begin{array}{c} CH_2COOR^5 \\ | \\ CHOR^4 \\ | \\ CH_2-N^+\!\!\!<\!\!\!\begin{array}{c}CH_3\\CH_3\\CH_3\end{array} \quad X^- \end{array}$$

| Example No. | $R^4$ | $R^5$ | $X^-$ | Physical properties |
|---|---|---|---|---|
| 13 | $-COCH_2CH_3$ | $-(CH_2)_2CH_3$ | $Cl^-$ | IR(Neat) cm$^{-1}$: 1740 NMR(CDCl$_3$)δ: 0.94(3H, t, J=7.4Hz), 1.15(3H, t, J=7.5 Hz), 1.65(2H, tq, J=6.8, 7.4Hz), 2.38(2H, q, J=7.6Hz), 2.80(1H, dd, J=17, 6.0Hz), 2.88 (1H, dd, J=17, 6.7Hz), 3.53(9H, s), 4.05(2H, t, J=6.7Hz), 4.09(1H, dd, J=14, 8.9Hz), 4.34 (1H, d, J=13Hz), 5.65 to 5.75(1H, m) |
| 14 | $-COCH_2CH_3$ | $-(CH_2)_{10}CH_3$ | $Cl^-$ | IR(Nujol)cm$^-$1: 1740 NMR(CDCl$_3$)δ: 0.88(3H, t, J=6.9Hz), 1.15(3H, t, J=7.5 Hz), 1.26(16H, br s), 1.55 to 1.65(2H, m), 2.38(2H, q, J=7.5 Hz), 2.79(1H, dd, J=17, 6.0 Hz), 2.87(1H, dd, J=17, 6.6 Hz), 3.53(9H, s), 4.00 to 4.10(3H, m), 4.32(1H, d, J=14 Hz), 5.65 to 5.75(1H, m) |

EXAMPLE 15

By processing (R)-(3-carboxy-2-propionyloxypropyl) trimethylammonium chloride and 1-bromoundecane in the same manner as described in Example 1 (except for using a saturated aqueous sodium nitrate solution in place of a saturated saline solution and changing the reaction time to 20 minutes), (R)-(3-undecyloxycarbonyl-2-propionyloxypropyl)-trimethylammonium nitrate was obtained.

m.p.: 68° to 70° C.

IR (Nujol) cm$^{-1}$: 1740

NMR (CDCl$_3$) δ: 0.88 (3H, t, J=6.9Hz), 1.14 (3H, t, J=7.5Hz), 1.25 (16H, br s), 1.55 to 1.65 (2H, m), 2.39 (2H, q, J=7.5Hz), 2.75 (1H, dd, J=17, 5.9Hz), 2.82 (1H, dd, J=17, 6.7Hz), 3.35 (9H, s), 4.00 to 4.10 (4H, m), 5.60 to 5.70 (1H, m)

EXAMPLE 16

By processing (R)-(3-carboxy-2-propionyloxypropyl) trimethylammonium chloride and 1-bromotridecane in the same manner as described in Example 1 (except for using a saturated aqueous sodium nitrate solution in place of a saturated saline solution), (R)-(2-propionyloxy-3-tridecyloxycarbonylpropyl)trimethylammonium nitrate was obtained.

m.p.: 79° to 80° C.

IR (Nujol) cm$^{-1}$: 1740

NMR (CDCl$_3$) δ: 0.88 (3H, t, J=7.0Hz), 1.14 (3H, t, J=7.3Hz), 1.26 (20H, br s), 1.55 to 1.65 (2H, m), 2.39 (2H, q, J=7.3Hz), 2.75 (1H, dd, J=17, 5.9Hz), 2.82 (1H, dd, J=17, 6.6Hz), 3.35 (9H, s), 4.00 (2H, d, J=5.1Hz), 4.00 to 4.10 (2H, m), 5.60 to 5.70 (1H, m)

EXAMPLE 17

By processing (R)-(3-carboxy-2-propionyloxypropyl) trimethylammonium chloride and 1-pentadecanol in the same manner as described in Example 3 (except for treating the extract with an aqueous sodium nitrate solution), (R)-(2-propionyloxy-3-pentadecyloxycarbonylpropyl) trimethylammonium nitrate was obtained.

m.p.: 83.5° to 84.5° C.

IR (Nujol) cm$^{-1}$: 1740

NMR (CDCl$_3$) δ: 0.88 (3H, t, J=7.0Hz), 1.14 (3H, t, J=7.6Hz), 1.26 (24H, br s), 1.55 to 1.65 (2H, m), 2.39 (2H, q, J=7.7Hz), 2.75 (1H, dd, J=17, 5.9Hz), 2.82 (1H, dd, J=17, 6.6Hz), 3.35 (9H, s), 4.00 to 4.10 (4H, m), 5.60 to 5.70 (1H, m)

EXAMPLES 18 to 26

By processing corresponding starting compounds in the same manner as described in Example 1, 3 or 15, the compounds shown in the following Table 6 were obtained.

TABLE 6

$$\begin{array}{c} CH_2COOR^5 \\ | \\ CHOR^4 \\ | \\ CH_2-N^+(CH_3)_3 \end{array} \quad X^-$$

| Example No. | R$^4$ | R$^5$ | X$^-$ | Physical properties |
|---|---|---|---|---|
| 18 | —COCH(CH$_3$)$_2$ | —(CH$_2$)$_{12}$CH$_3$ | NO$_3^-$ | m.p.: 106 to 110° C. IR(Nujol)cm$^{-1}$: 1740 NMR(CDCl$_3$)δ: 0.88 (3H, t, J=7.0Hz), 1.17(6H, d, J=7.0 Hz), 1.26(20H, br s), 1.55 to 1.65(2H, m), 2.59(1H, sept, J=7.0Hz), 2.74(1H, dd, J=17, 5.5Hz), 2.82(1H, dd, J=17, 6.6Hz), 3.35(9H, s), 4.00 to 4.10(4H, m), 5.60 to 5.70(1H, m) |
| 19 | —CO(CH$_2$)$_3$CH$_3$ | —(CH$_2$)$_2$CH$_3$ | Cl$^-$ | IR(Neat)cm$^{-1}$: 1740 NMR(CDCl$_3$)δ: 0.91 (3H, t, J=7.0Hz), 0.93(3H, t, J=7.0 Hz), 1.25 to 1.39 (2H, m), 1.54 to 1.71 (4H, m), 2.35(2H, t, J=7.0Hz), 2.81(1H, dd, J=17, 5.9Hz), 2.89(1H, dd, J=17, 6.3Hz), 3.48(9H, s), 4.00 to 4.08(3H, m), 4.26(1H, br d), 5.65 to 5.72(1H, m) |
| 20 | —CO(CH$_2$)$_3$CH$_3$ | —(CH$_2$)$_6$CH$_3$ | Cl$^-$ | IR(Neat)cm$^{-1}$: 1740 NMR(CDCl$_3$)δ: 0.89 (3H, t, J=7.0Hz), 0.91(3H, t, J=7.3 Hz), 1.20 to 1.40 (10H, m), 1.50 to |

TABLE 6-continued $$\begin{array}{c} CH_2COOR^5 \\ | \\ CHOR^4 \quad CH_3 \\ | \quad \diagdown \\ CH_2-N^+ \!\!-\!\! CH_3 \quad X^- \\ \diagup \\ CH_3 \end{array}$$

| Example No. | R⁴ | R⁵ | X⁻ | Physical properties |
|---|---|---|---|---|
| | | | | 1.65(4H, m), 2.35 (2H, t, J=7.3Hz), 2.79(1H, dd, J=18, 5.8Hz), 2.87(1H, dd, J=17, 6.6Hz), 3.53 (9H, s), 4.00 to 4.10 (3H, m), 4.33(1H, d, J=14Hz), 5.60 to 5.70 (1H, m) |
| 21 | —CO(CH₂)₃CH₃ | —(CH₂)₈CH₃ | NO₃⁻ | m.p.: 49 to 53° C. IR(Nujol)cm⁻¹: 1740 NMR(CDCl₃)δ: 0.88(3H, t, J=6.8Hz), 0.91(3H, t, J=7.3 Hz), 1.27 to 1.43(14H, m), 1.54 to 1.65(4H, m), 2.35(2H, t, J=7.6Hz), 2.76(1H, dd, J=17, 5.7Hz), 2.81 (1H, dd, J=17, 6.6Hz), 3.34(9H, s), 3.94 to 4.13(4H, m), 5.62 to 5.69(1H, m) |
| 22 | —CO(CH₂)₃CH₃ | —(CH₂)₁₀CH₃ | Cl⁻ | IR(Neat)cm⁻¹: 1740 NMR(CDCl₃)δ: 0.88(3H, t, J=7.0Hz), 0.91(3H, t, J=7.3 Hz), 1.20 to 1.40(18H, m), 1.50 to 1.70(4H, m), 2.34(2H, t, J=7.1Hz), 2.79(1H, dd, J=17, 6.0Hz), 2.87 (1H, dd, J=17, 6.7Hz), 3.52(9H, s), 4.00 to 4.10(3H, m), 4.31(1H, d, J=14Hz), 5.60 to 5.70 (1H, m) |
| 23 | —CO(CH₂)₃CH₃ | —(CH₂)₁₀CH₃ | NO₃⁻ | m.p.: 61 to 64° C. IR(Nujol)cm⁻¹: 1740 NMR(CDCl₃)δ: 0.88 (3H, t, J=6.7Hz), 0.91(3H, t, J=7.3 Hz), 1.26 to 1.40(18H, m), 1.54 to 1.64(4H, m), 2.35(2H, t, J=7.5Hz), 2.76(1H, dd, J=17, 5.8Hz), 2.81 (1H, dd, J=17, 6.6Hz), 3.35(9H, s), 3.94 to 4.13(4H, m), 5.62 to 5.70(1H, m) |
| 24 | —CO(CH₂)₃CH₃ | —(CH₂)₁₁CH₃ | Cl⁻ | m.p.: >60° C. IR(Nujol)cm⁻¹: 1740 NMR(CDCl₃)δ: 0.88(3H, t, J=6.7Hz), 0.91(3H, t, J=7.3 Hz), 1.20 to 1.40(20H, m), 1.54 to 1.64(4H, m), 2.32 to 2.37(2H, m), 2.80(1H, dd, J=17, 5.9 Hz), 2.85 (1H, dd, J=17, 6.7Hz), 3.53(9H, s), 4.03 to 4.12(3H, m), 4.31(1H, br d), 5.64 to 5.71(1H, m) |
| 25 | —CO(CH₂)₃CH₃ | —(CH₂)₁₂CH₃ | Cl⁻ | IR(Neat)cm⁻¹: 1740 NMR(CDCl₃)δ: 0.88(3H, t, J=6.7Hz), 0.91(3H, t, J=7.3 Hz), 1.20 to 1.39(22H, m), 1.54 to 1.64(4H, m), 2.35(2H, t, J=7.5Hz), 2.75 to |

TABLE 6-continued $$\begin{array}{c} CH_2COOR^5 \\ | \\ CHOR^4 \\ | \\ CH_2-N^+ \begin{array}{l} CH_3 \\ CH_3 \\ CH_3 \end{array} \end{array} \quad .X^-$$

| Example No. | R⁴ | R⁵ | X⁻ | Physical properties |
|---|---|---|---|---|
| 26 | —CO(CH₂)₃CH₃ | —(CH₂)₁₂CH₃ | NO₃⁻ | 2.91(2H, m), 3.52(9H, s), 4.01 to 4.13(3H, m), 4.28(1H, br d), 5.64 to 5.71(1H, m) m.p.: 68 to 70° C. IR(Nujol)cm⁻¹: 1740 NMR(CDCl₃)δ: 0.88 (3H, t, J=6.7Hz), 0.91 (3H, t, J=7.3Hz), 1.20 to 1.40(22H, m), 1.54 to 1.66(4H, m), 2.35 (2H, t, J=7.5Hz), 2.76 (1H, dd, J=17, 5.8Hz), 2.81(1H, dd, J=17, 6.7 Hz), 3.34(9H, s), 3.96 to 4.13(4H, m), 5.61 to 5.69(1H, m) |

EXAMPLE 27

By processing (R)-(3-carboxy-2-pentanoyloxypropyl) trimethylammonium chloride and 1-bromotridecane in the same manner as described in Example 1 (except for using a saturated aqueous sodium sulfonate solution in place of a saturated saline solution), (R)-(3-tridecyloxycarbonyl-2-pentanoyloxypropyl)trimethylammonium hemisulfonate was obtained.

m.p.: >57° C.
IR (Nujol) cm⁻¹: 1740

NMR (CDCl₃) δ: 0.88 (3H, t, J=6.9Hz), 0.90 (3H, t, J=7.3Hz), 1.26 to 1.38 (22H, m), 1.50 to 1.61 (4H, m), 2.29 (2H, t, J=7.6Hz), 2.83 (1H, dd, J=17, 7.2Hz), 3.08 (1H, dd, J=17, 4.5Hz), 3.44 (9H, s), 3.76 (1H, dd, J=14, 9.6Hz), 3.95 to 4.03 (2H, m), 4.51 (1H, br d), 5.69 to 5.77 (1H, m)

EXAMPLES 28 to 74

By processing corresponding starting compounds in the same manner as described in Example 1, 3, 6, 15, 17 or 27, the compounds shown in the following Table 7 were obtained.

TABLE 7

$$\begin{array}{c} CH_2COOR^5 \\ | \\ CHOR^4 \\ | \\ CH_2-N^+ \begin{array}{l} CH_3 \\ CH_3 \\ CH_3 \end{array} \end{array} \quad .X^-$$

| Example No. | R⁴ | R⁵ | X⁻ | Physical properties |
|---|---|---|---|---|
| 28 | —CO(CH₂)₃CH₃ | —(CH₂)₁₄CH₃ | NO₃⁻ | m.p.: 75 to 77° C. IR(Nujol) cm⁻¹: 1740 NMR(CDCl₃)δ: 0.88 (3H, t, J=6.9Hz), 0.91 (3H, t, J=7.2Hz), 1.26 (26H, br s), 1.55 to 1.65(4H, m), 2.35 (2H, t, J=7.3Hz), 2.75 (1H, dd, J=17, 5.7Hz), 2.82(1H, dd, J=17, 6.7Hz), 3.34(9H, s), 3.95 to 4.10(4H, m), 5.60 to 5.70(1H, m) |
| 29 | —CO(CH₂)₄CH₃ | —(CH₂)₁₀CH₃ | NO₃⁻ | m.p.: 46 to 50° C. IR(Nujol)cm⁻¹: 1740 NMR(CDCl₃)δ: 0.88 (3H, t, J=6.9Hz), 0.89 (3H, t, J=6.8Hz), 1.26 (20H, br s), 1.55 to 1.65(4H, m), 2.34 (2H, t, J=7.3Hz), 2.75 (1H, dd, J=17, 5.8Hz), 2.82(1H, dd, J=17, |

TABLE 7-continued $$\begin{array}{c} CH_2COOR^5 \\ | \\ CHOR^4 \\ | \\ CH_2-N^+\!\!\!<\!\!\!\begin{array}{c}CH_3\\CH_3\\CH_3\end{array} \cdot X^- \end{array}$$

| Example No. | R⁴ | R⁵ | X⁻ | Physical properties |
|---|---|---|---|---|
| | | | | 6.7Hz), 3.34(9H, s), 3.95 to 4.10(4H, m), 5.60 to 5.70(1H, m) |
| 30 | —CO(CH₂)₂CH(CH₃)₂ | —(CH₂)₁₀CH₃ | Cl⁻ | IR(Nujol)cm⁻¹: 1740 NMR(CDCl₃)δ: 0.89 (6H, d, J=8.3Hz), 0.85 to 0.90(3H, m), 0.85 to 0.90(3H, m), 1.26 (16H, br s), 1.45 to 1.64(5H, m), 2.30 to 2.40(2H, m), 2.79 (1H, dd, J=17, 5.9Hz), 2.87(1H, dd, J=17, 6.7Hz), 3.53(9H, s), 4.00 to 4.10(3H, m) 4.34(1H, d, J=13Hz), 5.60 to 5.70(1H, m) |
| 31 | —CO(CH₂)₂CH(CH₃)₂ | —(CH₂)₁₀CH₃ | NO₃⁻ | m.p.: 58 to 60° C. IR(Nujol)cm⁻¹: 1740 NMR(CDCl₃)δ: 0.86 to 0.91(9H, m), 1.26 (16H, br s), 1.46 to 1.66(5H, m), 2.32 to 2.38(2H, m), 2.76 (1H, dd, J=17, 5.8Hz), 2.81(1H, dd, J=17, 6.7Hz), 3.35(9H, s), 3.93 to 4.13(4H, m), 5.62 to 5.70(1H, m) |
| 32 | —CO(CH₂)₂CH(CH₃)₂ | —(CH₂)₁₁CH₃ | NO₃⁻ | m.p.: 67 to 69° C. IR(Nujol)cm⁻¹: 1740 NMR(CDCl₃)δ: 0.86 to 0.91(9H, m), 1.26 (18H, br s), 1.46 to 1.65(5H, m), 2.32 to 2.38(2H, m), 2.76 (1H, dd, J=17, 5.7Hz), 2.81(1H, dd, J=17, 6.7Hz), 3.35(9H, s), 3.94 to 4.13(4H, m), 5.62 to 5.69(1H, m) |
| 33 | —CO(CH₂)₂CH(CH₃)₂ | —(CH₂)₁₂CH₃ | NO₃⁻ | m.p.: 64 to 67° C. IR(Nujol)cm⁻¹: 1740 NMR(CDCl₃)δ: 0.88 (3H, t, J=6.9Hz), 0.90 (6H, d, J=6.2Hz), 1.26(20H, br s), 1.45 to 1.65(5H, m), 2.35 (2H, t, J=7.3Hz), 2.75 (1H, dd, J=17, 5.9 Hz), 2.82(1H, dd, J=17, 6.8Hz), 3.35 (9H, s), 3.95 to 4.10 (4H, m), 5.60 to 5.70 (1H, m) |
| 34 | —CO(CH₂)₅CH₃ | —(CH₂)₄CH₃ | Cl⁻ | IR(Neat)cm⁻¹: 1740 NMR(CDCl₃)δ: 0.86 to 0.93(6H, m), 1.26 to 1.36(10H, m), 1.55 to 1.66(4H, m), 2.31 to 2.36(2H, m), 2.80(1H, dd, J=17, 5.9Hz), 2.86(1H, dd, J=17, 6.6Hz), 3.52 (9H, s), 4.02 to 4.13 (3H, m), 4.32(1H, br d), 5.64 to 5.72(1H, m) |
| 35 | —CO(CH₂)₅CH₃ | —(CH₂)₈CH₃ | Cl⁻ | IR(Neat)cm⁻¹: 1740 |

TABLE 7-continued $$\begin{array}{c} CH_2COOR^5 \\ | \\ CHOR^4 \\ | \\ CH_2-N^+\begin{array}{c}CH_3\\CH_3\\CH_3\end{array} \quad . X^- \end{array}$$

| Example No. | R⁴ | R⁵ | X⁻ | Physical properties |
|---|---|---|---|---|
|  |  |  |  | NMR(CDCl₃)δ: 0.86 to 0.91(6H, m), 1.21 to 1.36(18H, m), 1.55 to 1.65(4H, m), 2.31 to 2.36(2H, m), 2.79(1H, dd, J=17, 5.9Hz), 2.86(1H, dd, J=17, 6.6Hz), 3.52 (9H, m), 4.31(1H, br d), 5.64 to 5.71(1H, m) |
| 36 | —CO(CH₂)₅CH₃ | —(CH₂)₈CH₃ | NO₃⁻ | m.p.: <34° C. IR(Neat)cm⁻¹: 1740 NMR(CDCl₃)δ: 0.86 to 0.91(6H, m), 1.27 to 1.29(18H, m), 1.58 to 1.62(4H, m), 2.35(2H, t, J=7.6 Hz), 2.76(1H, dd, J=17, 5.8Hz), 2.81 (1H, dd, J=17, 6.7 Hz), 3.34(9H, s), 3.93 to 4.13(4H, m), 5.62 to 5.70(1H, m) |
| 37 | —CO(CH₂)₅CH₃ | —(CH₂)₁₀CH₃ | NO₃⁻ | m.p.: 42 to 47° C. IR(Nujol)cm⁻¹: 1740 NMR(CDCl₃)δ: 0.85 to 0.90(6H, m), 1.26 (22H, br s), 1.55 to 1.75(4H, m), 2.34 (2H, t, J=7.3Hz), 2.75(1H, dd, J=17, 5.8Hz), 2.82(1H, dd, J=17, 6.6Hz), 3.34 (9H, s), 3.95 to 4.10 (4H, m), 5.60 to 5.70 (1H, m) |
| 38 | —CO(CH₂)₅CH₃ | —(CH₂)₁₂CH₃ | NO₃⁻ | m.p.: 56 to 57° C. IR(Nujol)cm⁻¹: 1740 NMR(CDCl₃)δ: 0.86 to 0.91(6H, m), 1.26 to 1.29(26H, m), 1.55 to 1.65(4H, m), 2.35(2H, t, J=7.6 Hz), 2.76(1H, dd, J=17, 5.7Hz), 2.80 (1H, dd, J=17, 6.6 Hz), 3.34(9H, s), 3.94 to 4.13(4H, m), 5.62 to 5.69(1H, m) |
| 39 | —CO(CH₂)₅CH₃ | —(CH₂)₁₄CH₃ | Cl⁻ | m.p.: <65° C. IR(Nujol)cm⁻¹: 1740 NMR(CDCl₃)δ: 0.85 to 0.91(6H, m), 1.26 to 1.29(30H, m), 1.55 to 1.65(4H, m), 2.31 to 2.36(2H, m), 2.74 to 2.91(2H, m), 3.52(9H, s), 4.01 to 4.13(3H, m), 4.31 (1H, br d), 5.64 to 5.71(1H, m) |
| 40 | —CO(CH₂)₅CH₃ | —(CH₂)₁₄CH₃ | ½SO₄²⁻ | m.p.: <120° C. IR(Nujol)cm⁻¹: 1740, 1735 NMR(CDCl₃)δ: 0.88(6H, t, J=6.6Hz), 1.26(30H, br s), 1.56 to 1.61(4H, m), |

TABLE 7-continued $$\begin{array}{c} CH_2COOR^5 \\ | \\ CHOR^4 \\ | \\ CH_2-N^+ \begin{array}{c} CH_3 \\ CH_3 \\ CH_3 \end{array} \cdot X^- \end{array}$$

| Example No. | $R^4$ | $R^5$ | $X^-$ | Physical properties |
|---|---|---|---|---|
| | | | | 2.27(2H, t, J=7.6Hz), 2.83(1H, dd, J=17, 7.3 Hz), 3.11(1H, dd, J=17, 4.8Hz), 3.47(9H, s), 3.76 (1H, dd, J=14, 9.3Hz), 3.93 to 4.05(2H, m), 4.66 (1H, br d), 5.70 to 5.78 (1H, m) |
| 41 | $-CO(CH_2)_7CH_3$ | $-(CH_2)_8CH_3$ | $Cl^-$ | m.p.: 45 to 60° C. IR(Nujol)cm$^{-1}$: 1740 NMR(CDCl$_3$)δ: 0.88 (6H, t, J=7.0Hz), 1.27 (22H, br s), 1.55 to 1.65(4H, m), 2.33 (2H, t, J=7.6Hz), 2.79 (1H, dd, J=17, 5.8Hz), 2.87(1H, dd, J=17, 6.7Hz), 3.51(9H, s), 4.00 to 4.10(3H, m), 4.33(1H, d, J=14Hz), 5.60 to 5.70(1H, m) |
| 42 | $-CO(CH_2)_7CH_3$ | $-(CH_2)_{10}CH_3$ | $Cl^-$ | m.p.: <60° C. IR(Neat)cm$^{-1}$: 1740 NMR(CDCl$_3$)δ: 0.88 (6H, t, J=6.7Hz), 1.27 (26H, br s), 1.54 to 1.65(4H, m), 2.30 to 2.35(2H, m), 2.80 (1H, dd, J=17, 5.9Hz), 2.85(1H, dd, J=17, 6.7Hz), 3.53(9H, m), 4.34(1H, br d), 5.64 to 5.71(1H, m) |
| 43 | $-CO(CH_2)_9CH_3$ | $-(CH_2)_2CH_3$ | $Cl^-$ | IR(Neat)cm$^{-1}$: 1735 NMR(CDCl$_3$)δ: 0.88 (3H, t, J=6.7Hz), 0.93(3H, t, J=7.4 Hz), 1.26(14H, br s), 1.55 to 1.71(4H, m), 2.33(2H, t, J= 7.5Hz), 2.80(1H, dd, J=17, 5.6Hz), 2.87 (1H, dd, J=17, 6.2 Hz), 3.53(9H, s), 4.01 to 4.10(3H, m), 4.34(1H, br d), 5.65 to 5.72(1H, m) |
| 44 | $-CO(CH_2)_9CH_3$ | $-(CH_2)_4CH_3$ | $Cl^-$ | IR(Neat)cm$^{-1}$: 1745 NMR(CDCl$_3$)δ: 0.86 to 0.93(6H, m), 1.26 to 1.34(18H, m), 1.55 to 1.67(4H, m), 2.30 to 2.36(2H, m), 2.80(1H, dd), J=17, 5.9Hz), 2.86(1H, dd, J=17, 6.6Hz), 3.51 (9H, s), 4.01 to 4.11 (3H, m), 4.31(1H, br d), 5.64 to 5.71(1H, m) |
| 45 | $-CO(CH_2)_9CH_3$ | $-(CH_2)_4CH_3$ | $NO_3^-$ | m.p.: 61 to 63° C. IR(Nujol)cm$^{-1}$: 1740 NMR(CDCl$_3$)δ: 0.88 (3H, t, J=7.0Hz), 0.91(3H, t, J=6.8 Hz), 1.26(18H, br s), 1.55 to 1.65(4H, m), 2.34(2H, t, J= |

TABLE 7-continued $$\begin{array}{c} CH_2COOR^5 \\ | \\ CHOR^4 \\ | \\ CH_2-N^+ \begin{array}{c} CH_3 \\ CH_3 \\ CH_3 \end{array} \end{array} \cdot X^-$$

| Example No. | R⁴ | R⁵ | X⁻ | Physical properties |
|---|---|---|---|---|
| 46 | —CO(CH₂)₉CH₃ | —CH₂CH(CH₃)CH₂CH₃ | Cl⁻ | 7.0Hz), 2.75(1H, dd, J=17, 5.7Hz), 2.82 (1H, dd, J=17, 6.7 Hz), 3.34(9H, s), 3.95 to 4.15(4H, m), 5.60 to 5.70(1H, m) IR(Neat)cm⁻¹: 1740 NMR(CDCl₃)δ: 0.85 to 0.95(9H, m), 1.10 to 1.80(19H, m), 2.32 (2H, t, J=7.2Hz), 2.80 (1H, dd, J=17, 5.4Hz), 2.88(1H, dd, J=17, 6.0Hz), 3.52(9H, s), 3.85 to 4.00(2H, m), 4.08(1H, dd, J=14, 8.8Hz), 4.36(1H, d, J=15Hz), 5.60 to 5.70 (1H, m) |
| 47 | —CO(CH₂)₉CH₃ | —(CH₂)₆CH₃ | Cl⁻ | m.p.: >65° C. IR(Nujol)cm⁻¹: 1740, 1730 NMR(CDCl₃)δ: 0.85 to 0.91(6H, m), 1.26 to 1.34(22H, m), 1.55 to 1.66(4H, m), 2.30 to 2.36(2H, m), 2.80 (1H, dd, J=17, 5.9Hz), 2.86(1H, dd, J=17, 6.6Hz), 3.51(9H, s), 4.02 to 4.11(3H, m), 4.31(1H, br d), 5.64 to 5.71(1H, m) |
| 48 | —CO(CH₂)₉CH₃ | —(CH₂)₈CH₃ | Cl⁻ | m.p.: >65° C. IR(Neat)cm⁻¹: 1740 NMR(CDCl₃)δ: 0.88 (6H, t, J=6.7Hz), 1.26 (26H, br s), 1.54 to 1.64(4H, m), 2.30 to 2.35(2H, m), 2.80 (1H, dd, J=17, 5.9Hz), 2.85(1H, dd, J=17, 6.7Hz), 3.53(9H, s), 4.01 to 4.13(3H, m), 4.33(1H, br d), 5.64 to 5.71(1H, m) |
| 49 | —CO(CH₂)₉CH₃ | —(CH₂)₁₀CH₃ | Cl⁻ | m.p.: 135 to 136° C. IR(Nujol)cm⁻¹: 1730, 1720 NMR(CDCl₃)δ: 0.88(6H, t, J=6.7Hz), 1.26(30H, br s), 1.54 to 1.65(4H, m), 2.31 to 2.36(2H, m), 2.80(1H, dd, J=17, 5.8Hz), 2.86(1H, dd, J=17, 6.7Hz), 3.52(9H, s), 4.01 to 4.13(3H, m), 4.32 (1H, br d), 5.64 to 5.71(1H, m) |
| 50 | —CO(CH₂)₈CH=CH₂ | —(CH₂)₄CH₃ | Cl⁻ | IR(Nujol)cm⁻¹: 1740 NMR(CDCl₃)δ: 0.91(3H, t, J=7.0Hz), 1.28(14H, br s), 1.55 to 1.65(4H, m), 2.00 to 2.10(2H, m), 2.36(2H, t, J=7.6 Hz), 2.79(1H, dd, J=17, 5.7Hz), 2.86(1H, dd, |

TABLE 7-continued $$\begin{array}{c} CH_2COOR^5 \\ | \\ CHOR^4 \\ | \\ CH_2-N^+ \begin{array}{c} CH_3 \\ CH_3 \\ CH_3 \end{array} \end{array} \cdot X^-$$

| Example No. | $R^4$ | $R^5$ | $X^-$ | Physical properties |
|---|---|---|---|---|
| | | | | J=17, 6.7Hz), 3.52(9H, s), 4.00 to 4.10(3H, m), 4.34(1H, d, J=14 Hz), 4.90 to 5.05(2H, m), 5.60 to 5.70(1H, m), 5.81(1H, ddt, J=17, 10, 6.7Hz) |
| 51 | $-CO(CH_2)_8CH=CH_2$ | $-(CH_2)_{10}CH_3$ | $Cl^-$ | IR(Nujol)cm$^{-1}$: 1740 NMR(CDCl$_3$)δ: 0.88(3H, t, J=6.9Hz), 1.25 to 1.30(26H, br s), 1.55 to 1.65(4H, m), 2.00 to 2.10(2H, m), 2.33(2H, t, J=7.6Hz), 2.78(1H, dd, J=17, 5.9Hz), 2.86 (1H, dd, J=17, 6.7Hz), 3.52(9H, s), 4.00 to 4.10(3H, m), 4.32(1H, d, J=14Hz), 4.90 to 5.05 (2H, m), 5.60 to 5.70 (1H, m), 5.81(1H, ddt, J=17, 10, 6.7Hz) |
| 52 | $-CO(CH_2)_{11}CH_3$ | $-(CH_2)_2CH_3$ | $NO_3^-$ | m.p.: 54 to 56° C. IR(Nujol)cm$^{-1}$: 1740 NMR(CDCl$_3$)δ: 0.88(3H, t, J=6.9Hz), 0.93(3H, t, J=7.4Hz), 1.26(18H, br s), 1.55 to 1.70(4H, m), 2.34(2H, t, J=7.1 Hz), 2.76(1H, dd, J=17, 5.7Hz), 2.83(1H, dd, J=17, 6.8Hz), 3.34(9H, s), 3.95 to 4.10(4H, m), 5.60 to 5.70(1H, m) |
| 53 | $-CO(CH_2)_{11}CH_3$ | $-(CH_2)_4CH_3$ | $Cl^-$ | IR(Nujol)cm$^{-1}$: 1740 NMR(CDCl$_3$)δ: 0.88(3H, t, J=6.9Hz), 0.91(3H, t, J=6.9Hz), 1.20 to 1.35(22H, br s), 1.55 to 1.65(4H, m), 2.33 (2H, t, J=7.2Hz), 2.79 (1H, dd, J=17, 5.9Hz), 2.87(1H, dd, J=17, 6.6 Hz), 3.52(9H, s), 4.05 (1H, d, J=15Hz), 4.08 (2H, t, J=7.3Hz), 4.34 (1H, d, J=15Hz), 5.60 to 5.70(1H, m) |
| 54 | $-CO(CH_2)_{11}CH_3$ | $-(CH_2)_4CH_3$ | $NO_3^-$ | m.p.: 63 to 67° C. IR(Nujol)cm$^{-1}$: 1740 NMR(CDCl$_3$)δ: 0.89(3H, t, J=7.0Hz), 0.91(3H, t, J=6.8Hz), 1.26(22H, br s), 1.55 to 1.70(4H, m), 2.34(2H, d, J=7.3 Hz), 2.75(1H, dd, J=17, 5.7Hz), 2.82(1H, dd, J=17, 6.7Hz), 3.34(9H, s), 3.90 to 4.10(4H, m), 5.60 to 5.70(1H, m) |
| 55 | $-CO(CH_2)_{11}CH_3$ | $-(CH_2)_6CH_3$ | $Cl^-$ | m.p.: 70 to 75° C. IR(Nujol)cm$^{-1}$: 1740 NMR(CDCl$_3$)δ: 0.88 to 0.90(6H, m), 1.26(26H, br s), 1.50 to 1.70(4H, m), 2.33(2H, t, J=7.5 Hz), 2.78(1H, dd, J=17, 5.9Hz), 2.86(1H, dd, J= 17, 6.7Hz), 3.52(9H, |

TABLE 7-continued $$\begin{array}{c} CH_2COOR^5 \\ | \\ CHOR^4 \\ | \\ CH_2-N^+ \genfrac{}{}{0pt}{}{CH_3}{\genfrac{}{}{0pt}{}{CH_3}{CH_3}} \end{array} \cdot X^-$$

| Example No. | R⁴ | R⁵ | X⁻ | Physical properties |
|---|---|---|---|---|
| | | | | s), 4.00 to 4.10(3H, m), 4.34(1H, d, J=13 Hz), 5.60 to 5.70(1H, m) |
| 56 | —CO(CH₂)₁₁CH₃ | —(CH₂)₈CH₃ | Cl⁻ | m.p.: 134 to 136° C. IR(Nujol)cm⁻¹: 1740 NMR(CDCl₃)δ: 0.88(6H, t, J=7.0Hz), 1.26(30H, br s), 1.50 to 1.65(4H, m), 2.33(2H, t, J=7.5 Hz), 2.78(1H, dd, J=17, 5.9Hz), 2.86(1H, dd, J=17, 6.6Hz), 3.53(9H, s), 4.00 to 4.10(3H, m), 4.34(1H, d, J=14 Hz), 5.60 to 5.70(1H, m) |
| 57 | —CO(CH₂)₁₁CH₃ | —(CH₂)₂₀CH₃ | Cl⁻ | m.p.: 151 to 152° C. IR(Nujol)cm⁻¹: 1730, 1720 NMR(CDCl₃)δ: 0.88(6H, t, J=6.7Hz), 1.26(54H, br s), 1.55 to 1.65(4H, m), 2.30 to 2.36(2H, m), 2.80(1H, dd, J=17, 5.9Hz), 2.85(1H, dd, J=17, 6.6Hz), 3.52(9H, s), 4.01 to 4.13(3H, m), 4.33(1H, br d), 5.64 to 5.71(1H, m) |
| 58 | —CO(CH₂)₁₂CH₃ | —(CH₂)₁₀CH₃ | Cl⁻ | m.p.: 119 to 125° C. IR(Nujol)cm⁻¹: 1740 NMR(CDCl₃)δ: 0.88(6H, t, J=6.9Hz), 1.26(36H, s), 1.50 to 1.70(4H, m), 2.33(2H, t, J=7.6 Hz), 2.78(1H, dd, J=17, 6.2Hz), 2.86(1H, dd, J=17, 6.7Hz), 3.52(9H, s), 4.00 to 4.10(3H, m), 4.33(1H, d, J=14 Hz), 5.60 to 5.70(1H, m) |
| 59 | —CO(CH₂)₁₃CH₃ | —(CH₂)₁₀CH₃ | NO₃⁻ | m.p.: 84 to 86° C. IR(Nujol)cm⁻¹: 1740 NMR(CDCl₃)δ: 0.88(3H, t, J=6.6Hz), 1.26(38H, br s), 1.55 to 1.65(4H, m), 2.34(2H, t, J=7.7 Hz), 2.76(1H, dd, J=17, 5.9Hz), 2.80(1H, dd, J=17, 6.5Hz), 3.34(9H, s), 3.93 to 4.13(4H, m), 5.61 to 5.70(1H, m) |

TABLE 7-continued

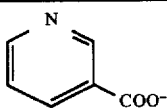

| Example No. | $R^4$ | $R^5$ | $X^-$ | Physical properties |
|---|---|---|---|---|
| 60 | $-CO(CH_2)_{13}CH_3$ | $-(CH_2)_{10}CH_3$ | pyridine-3-COO$^-$ | IR(Neat)cm$^{-1}$: 1740, 1600 NMR(CDCl$_3$)δ: 0.88(6H, t, J=6.8Hz), 1.25(38H, br s), 1.57 to 1.63(4H, m), 2.25 to 2.31(2H, m), 2.72 to 2.88(2H, m), 3.48(9H, s), 3.97 to 4.18(3H, m), 4.33 (1H, br d), 5.63 to 5.70 (1H, m), 8.31(1H, dt, J=7.8, 2.0Hz), 8.55(1H, dd, J=4.8, 2.0Hz), 9.22 (1H, d, J=1.3Hz) |
| 61 | $-CO(CH_2)_{14}CH_3$ | $-(CH_2)_2CH_3$ | Cl$^-$ | m.p.: ~147° C. IR(Nujol)cm$^{-1}$: 1735 NMR(CDCl$_3$)δ: 0.88(3H, t, J=6.6Hz), 0.93(3H, t, J=7.3Hz), 1.25(24H, br s), 1.54 to 1.71(4H, m), 2.31 to 2.36(2H, m), 2.81(1H, dd, J=17, 5.9Hz), 2.87(1H, dd, J=17, 6.6Hz), 3.51(9H, s), 4.01 to 4.10(3H, m), 4.32(1H, br d), 5.64 to 5.72(1H, m) |
| 62 | $-CO(CH_2)_{14}CH_3$ | $-(CH_2)_4CH_3$ | Cl$^-$ | IR(Neat)cm$^{-1}$: 1740 NMR(CDCl$_3$)δ: 0.88(3H, t, J=6.7Hz), 0.91(3H, t, J=6.8Hz), 1.26 to 1.37(28H, m), 1.55 to 1.66(4H, m), 2.27 to 2.35(4H, m), 2.80(1H, dd, J=17, 5.9Hz), 2.86 (1H, dd, J=17, 6.6Hz), 3.52(9H, s), 4.02 to 4.13(3H, m), 4.32(1H, br d), 5.64 to 5.71(1H, m) |
| 63 | $-CO(CH_2)_{14}CH_3$ | $-(CH_2)_8CH_3$ | Cl$^-$ | m.p.: >80° C. IR(Neat)cm$^{-1}$: 1740 NMR(CCl$_3$)δ: 0.86 to 0.90(6H, m), 1.26(36H, br s), 1.55 to 1.65(4H, m), 2.30 to 2.35(2H, m), 2.80(1H, dd, J=17, 5.9Hz), 2.85(1H, dd, J=17, 6.6Hz), 3.52(9H, s), 4.01 to 4.13(3H, m), 4.32(1H, br d), 5.64 to 5.71(1H, m) |
| 64 | $-CO(CH_2)_7CH=CHCH_2-$ $-CH=CH(CH_2)_4CH_3$ | $-(CH_2)_2CH_3$ | Cl$^-$ | IR(Neat)cm$^{-1}$: 1740 NMR(CDCl$_3$)δ: 0.89(3H, t, J=7.0Hz), 0.93(3H, t, J=7.4Hz), 1.20 to 1.40 (4H, m), 2.00 to 2.15 (4H, m), 2.33(2H, t, J= 7.7Hz), 2.77(2H, t, J= 5.5Hz), 2.75 to 2.90 (2H, m), 3.51(9H, s), 4.00 to 4.10(1H, m), 4.05(2H, t, J=6.8Hz), 4.34(1H, d, J=14Hz), 5.25 to 5.40(4H, m), 5.60 to 5.70(1H, m) |

TABLE 7-continued $$\begin{array}{c} CH_2COOR^5 \\ | \\ CHOR^4 \\ | \\ CH_2-N^+ \begin{array}{l} CH_3 \\ -CH_3 \\ CH_3 \end{array} \end{array} \cdot X^-$$

| Example No. | R⁴ | R⁵ | X⁻ | Physical properties |
|---|---|---|---|---|
| 65 | —COCH(CH₃)₂ | —(CH₂)₁₃CH₃ | NO₃⁻ | m.p.: 105 to 109° C. IR(Nujol)cm⁻¹: 1730 NMR(CDCl₃)δ: 0.88 (3H, t, J=6.9Hz), 1.17(6H, d, J=7.9 Hz), 1.26(22H, br s), 1.55 to 1.70(2H, m), 2.59(1H, sept, J= 7.0Hz), 2.74(1H, dd, J=18, 5.6Hz), 2.82(1H, dd, J=17, 6.6Hz), 3.35(9H, s), 4.00 to 4.10(4H, m), 5.60 to 5.70(1H, m) |
| 66 | —COCH(CH₂CH₂CH₃)₂ | —(CH₂)₉CH₃ | NO₃⁻ | IR(Neat)cm⁻¹: 1740 NMR(CDCl₃)δ: 0.88 (3H, t, J=6.9Hz), 0.89(3H, t, J=7.2 Hz), 1...18 to 1.66 (24H, m), 2.35 to 2.45(1H, m), 2.80 (2H, d, J=6.1Hz), 3.35(9H, s), 3.98 to 4.13(4H, m), 5.54 to 5.65(1H, m) |
| 67 | —COCH(CH₂CH₂CH₃)₂ | —(CH₂)₁₀CH₃ | NO₃⁻ | IR(Neat)cm⁻¹: 1740 NMR(CDCl₃)δ: 0.80 to 0.95(9H, m), 1.26 (20H, br s), 1.40 to 1.70(6H, m), 2.35 to 2.45(1H, m), 2.80 (2H, d, J=5.9Hz), 3.35 (9H, s), 4.00 to 4.10 (4H, m), 5.55 to 5.65 (1H, m) |
| 68 | —CO(CH₂)₁₁CH₃ | —CH(CH₂CH₃)₂ | NO₃⁻ | IR(Neat)cm⁻¹: 1740 NMR(CDCl₃)δ: 0.87 (6H, t, J=7.5Hz), 0.88 (3H, t, J=7.0Hz), 1.26 (18H, br s), 1.46 to 1.66(6H, m), 2.34 (2H, t, J=7.6Hz), 2.78 (1H, dd, J=17, 5.8Hz), 2.82(1H, dd, J=17, 6.5Hz), 3.35(9H, s), 3.95 to 4.06(2H, m), 4.71 to 4.79(1H, m), 5.62 to 5.70(1H, m) |
| 69 | —CO(CH₂)₁₁CH₃ | —CHCH₂CH₂CH₃<br>\|<br>CH₃ | NO₃⁻ | IR(Neat)cm⁻¹: 1740 NMR(CDCl₃)δ: 0.85 to 0.95(6H, m), 1.21 (3H, d, J=6.2Hz), 1.26 (20H, br s), 1.40 to 1.60(4H, m), 2.34 (2H, t, J=7.4Hz), 2.65 to 2.85(2H, m), 3.35 (9H, s), 3.90 to 4.10 (2H, m), 4.85 to 4.95 (1H, m), 5.60 to 5.70 (1H, m) |
| 70 | —CO(CH₂)₁₃CH₃ | —(CH₂)₂CH₃ | NO₃⁻ | m.p.: 60 to 62° C. IR(Nujol)cm⁻¹: 1740 NMR(CDCl₃)δ: 0.88(3H, |

TABLE 7-continued $$\begin{array}{c} CH_2COOR^5 \\ | \\ CHOR^4 \\ | \\ CH_2-N^+ \!\!\!\begin{array}{c} CH_3 \\ -CH_3 \\ CH_3 \end{array} \end{array} \cdot X^-$$

| Example No. | R⁴ | R⁵ | X⁻ | Physical properties |
|---|---|---|---|---|
| 71 | —CO(CH₂)₁₃CH₃ | —(CH₂)₄CH₃ | NO₃⁻ | t, J=6.7Hz), 0.93(3H, t, J=7.4Hz), 1.25(22H, br s), 1.54 to 1.71(4H, m), 2.34(2H, t, J=7.6 Hz), 2.77(1H, dd, J=17, 5.7Hz), 2.82(1H, dd, J=17, 6.7Hz), 3.34(9H, s), 3.93 to 4.10(4H, m), 5.62 to 5.70(1H, m) m.p.: 59 to 61° C. IR(Nujol)cm⁻¹: 1740 NMR(CDCl₃)δ: 0.88(3H, t, J=6.9Hz), 0.91(3H, t, J=6.9Hz), 1.25(26H, br s), 1.55 to 1.70(4H, m), 2.34(2H, t, d=7.2 Hz), 2.75(1H, dd, J=17, 5.8Hz), 2.82(1H, dd, J=17, 6.6Hz), 3.34(9H, s), 3.90 to 4.10(4H, m), 5.60 to 5.70(1H, m) |
| 72 | —CO(CH₂)₇CH₃ | —(CH₂)₄CH₃ | NO₃⁻ | m.p.: 62 to 64° C. IR(Nujol)cm⁻¹: 1740 NMR(CDCl₃)δ: 0.88(3H, t, J=6.8Hz), 0.91(3H, t, J=6.8Hz), 1.21 to 1.41(14H, m), 1.55 to 1.67(4H, m), 2.34(2H, t, J=7.6Hz), 2.76(1H, dd, J=17, 5.8Hz), 2.81 1H), dd, J=17, 6.7Hz), 3.34(9H, s), 3.93 to 4.13(4H, m), 5.62 to 5.70(1H, m) |
| 73 | —CO(CH₂)₇CH₃ | —(CH₂)₆CH₃ | NO₃⁻ | m.p.: 59 to 61° C. IR(Nujol)cm⁻¹: 1740 NMR(CDCl₃)δ: 0.86 to 0.91(6H, m), 1.27 to 1.31(18H, m), 1.55 to 1.65(4H, m), 2.34(2H, t, J=7.6 Hz), 2.76(1H, dd, J=17, 5.7Hz), 2.81 (1H, dd, J=17, 6.7 Hz), 3.34(9H, s), 3.93 to 4.13(4H, m), 5.62 to 5.70(1H, m) |
| 74 | —COCH(CH₃)₂ | —(CH₂)₁₄CH₃ | NO₃⁻ | m.p.: 107 to 110° C. IR(Nujol)cm⁻¹: 1735 NMR(CDCl₃)δ: 0.88 (3H, t, J=6.7Hz), 1.17(6H, br d), 1.26 (24H, br s), 1.56 to 1.65(2H, m), 2.58 (1H, sept, J=7.0Hz), 2.75(1H, dd, J=17, 5.8Hz), 2.81(1H, dd, J=17, 6.8Hz), 3.35 (9H, s), 3.97 to 4.13 (4H, m), 5.62 to 5.70 (1H, m) |

EXAMPLES 75 and 92

By processing corresponding starting compounds in the same manner as described in Example 15 or 17, the compounds shown in the following Table 8 were obtained.

TABLE 8

$$\begin{array}{c} CH_2COOR^5 \\ | \\ CHOR^4 \\ | \\ CH_2-N^+ \begin{pmatrix} CH_3 \\ CH_3 \\ CH_3 \end{pmatrix} \cdot NO_3^- \end{array}$$

| Example No. | R$^4$ | R$^5$ | Synthetic method |
|---|---|---|---|
| 75 | —COCH(CH$_3$)$_2$ | —(CH$_2$)$_9$CH=CH$_2$ | Example 17 |
| 76 | —CO(CH$_2$)$_2$CH(CH$_3$)$_2$ | —(CH$_2$)$_9$CH=CH$_2$ | Example 17 |
| 77 | —CO(CH$_2$)$_5$CH$_3$ | —(CH$_2$)$_9$CH=CH$_2$ | Example 17 |
| 78 | —CO(CH$_2$)$_9$CH$_3$ | —(CH$_2$)$_6$CH$_3$ | Example 15 |
| 79 | —CO(CH$_2$)$_9$CH$_3$ | —CH$_2$CH(CH$_2$CH$_2$CH$_3$)$_2$ | Example 17 |
| 80 | —CO(CH$_2$)$_{11}$CH$_3$ | —(CH$_2$)$_3$CH(CH$_3$)$_2$ | Example 17 |
| 81 | —CO(CH$_2$)$_{11}$CH$_3$ | —(CH$_2$)$_6$CH$_3$ | Example 15 |
| 82 | —CO(CH$_2$)$_{13}$CH$_3$ | —CH$_2$CH(CH$_3$)$_2$ | Example 15 |
| 83 | —CO(CH$_2$)$_4$CH$_3$ | —(CH$_2$)$_{12}$CH$_3$ | Example 17 |
| 84 | —CO(CH$_2$)$_{10}$CH$_3$ | —(CH$_2$)$_3$CO$_2$CH$_2$CH$_3$ | Example 15 |
| 85 | —CO(CH$_2$)$_5$CH$_3$ | —(CH$_2$)$_{12}$OH | Example 15 |
| 86 | —CO(CH$_2$)$_2$CO$_2$CH$_2$CH$_3$ | —(CH$_2$)$_{12}$CH$_3$ | Example 15 |
| 87 | —CO(CH$_2$)$_6$CH$_3$ | —(CH$_2$)$_{10}$CH$_3$ | Example 17 |
| 88 | —CO(CH$_2$)$_6$CH$_3$ | —(CH$_2$)$_{12}$CH$_3$ | Example 15 |
| 89 | —CO(CH$_2$)$_6$CH$_3$ | —(CH$_2$)$_{14}$CH$_3$ | Example 17 |
| 90 | —CO(CH$_2$)$_2$CO$_2$CH$_2$CH$_3$ | —(CH$_2$)$_{10}$CH$_3$ | Example 17 |
| 91 | —CO(CH$_2$)$_2$CO$_2$CH$_2$CH$_3$ | —(CH$_2$)$_{11}$CH$_3$ | Example 15 |
| 92 | —CO(CH$_2$)$_2$CO$_2$CH$_2$CH$_3$ | —(CH$_2$)$_{13}$CH$_3$ | Example 15 |

The physical properties of the compounds obtained in Examples 75 to 92 are shown below.

EXAMPLE 75

Resinous product

IR (Nujol) cm$^{-1}$: 1740

NMR (CDCl$_3$) δ: 1.16 (6H, d, J=7.0Hz), 1.28 (12H, br s), 1.55 to 1.65 (2H, m), 2.00 to 2.10 (2H, m), 2.59 (1H, sept, J=7.0Hz), 2.74 (1H, dd, J=17, 5.2Hz), 2.82 (1H, dd, J=17, 7.0Hz), 3.34 (9H, s), 4.00 to 4.10 (4H, m), 4.90 to 5.05 (2H, m), 5.60 to 5.70 (1H, m), 5.81 (1H, ddt, J=17, 10, 6.7Hz)

MS (ESI) m/z: 384 [(MH-HNO$_3$)$^+$]

EXAMPLE 76 m.p.: 51° to 53° C.

IR (Nujol) cm$^{-1}$: 1740, 1640

NMR (CDCl$_3$) δ: 0.89 (6H, d, J=6.2Hz), 1.29 to 1.43 (12H, m), 1.46 to 1.65 (5H, m), 2.00 to 2.08 (2H, m), 2.32 to 2.38 (2H, m), 2.76 (1H, dd, J=17, 5.7Hz), 2.81 (1H, dd, J=17, 6.7Hz), 3.34 (9H, s), 3.93 to 4.13 (4H, m), 4.90 to 5.03 (2H, m), 5.62 to 5.69 (1H, m), 5.81 (1H, ddt, J=17, 10, 6.6Hz)

MS (ESI) m/z: 412 [(MH-HNO$_3$)$^+$]

EXAMPLE 77

Resinous product

IR (Neat) cm$^{-1}$: 2920, 2850, 1740, 1640

NMR (CDCl$_3$) δ: 0.89 (3H, t, J=6.8Hz), 1.29 to 1.41 (18H, m), 1.55 to 1.65 (4H, m), 2.00 to 2.08 (2H, m), 2.34 (2H, t, J=7.6Hz), 2.76 (1H, dd, J=17, 5.7Hz), 2.81 (1H, dd, J=17, 6.6Hz), 3.34 (9H, s), 3.92 to 4.13 (4H, m), 4.90 to 5.03 (2H, m), 5.61 to 5.69 (1H, m), 5.81 (1H, ddt, J=17, 10, 6.7Hz)

MS (ESI) m/z: 426 [(MH-HNO$_3$)$^+$]

EXAMPLE 78 m.p.: 69° to 71° C.

IR (Nujol) cm$^{-1}$: 1740

NMR (CDCl$_3$) δ: 0.88 (3H, t, J=6.7Hz), 0.89 (3H, t, J=7.0 Hz), 1.26 (22H, br s), 1.55 to 1.66 (4H, m), 2.34 (2H, t, J=7.6Hz), 2.76 (1H, dd, J=17, 5.7Hz), 2.81 (1H, dd, J=17, 6.7Hz), 3.34 (9H, s), 3.93 to 4.13 (4H, m), 5.61 to 5.69 (1H, m)

MS (ESI) m/z: 428 [(MH-HNO$_3$)$^+$]

EXAMPLE 79

Resinous product

IR (Neat) cm$^{-1}$: 1740

NMR (CDCl$_3$) δ: 0.88 (3H, t, J=5.6Hz), 0.90 (6H, t, J=6.7 Hz), 1.26 (22H, br s), 1.55 to 1.70 (3H, m), 2.34 (2H, t, J=7.3Hz), 2.76 (1H, dd, J=17, 5.9Hz), 2.82 (1H, dd, J=17, 6.6Hz), 3.34 (9H, s), 3.95 to 4.10 (4H, m), 5.60 to 5.70 (1H, m)

MS (ESI) m/z: 442 [(MH-HNO$_3$)$^+$]

EXAMPLE 80

Resinous product

IR (Neat) cm$^{-1}$: 1740

NMR (CDCl$_3$) δ: 0.88 (3H, t, J=7.0Hz), 0.89 (6H, d, J=6.6 Hz), 1.26 (20H, br s), 1.50 to 1.70 (5H, m), 2.34 (2H, t, J=7.3Hz), 2.75 (1H, dd, J=17, 5.6Hz), 2.82 (1H, dd, J=17, 6.8Hz), 3.34 (9H, s), 3.95 to 4.10 (4H, m), 5.60 to 5.70 (1H, m)

MS (ESI) m/z: 442 [(MH-HNO$_3$)$^+$]

EXAMPLE 81 m.p.: 72° to 73° C.

IR (Nujol) cm$^{-1}$: 1740

NMR (CDCl$_3$) δ: 0.88 (3H, t, J=6.7Hz), 0.89 (3H, t, J=7.0 Hz), 1.26 (26H, br s), 1.54 to 1.66 (4H, m), 2.34 (2H, t, J=7.6Hz), 2.76 (1H, dd, J=17, 5.8Hz), 2.81 (1H, dd, J=17, 6.7Hz), 3.34 (9H, s), 3.92 to 4.13 (4H, m), 5.61 to 5.69 (1H, m)

MS (ESI) m/z: 456 [(MH-HNO$_3$)$^+$];

EXAMPLE 82

Resinous product

IR (Neat) cm$^{-1}$: 1740

NMR (CDCl$_3$) δ: 0.88 (3H, t, J=7.0Hz), 0.92 (6H, d, J=6.7 Hz), 1.26 (22H, br s), 1.55 to 1.65 (2H, m), 1.85 to 2.00 (1H, m), 2.34 (2H, t, J=7.9Hz), 2.77 (1H, dd, J=17, 5.9Hz), 2.84 (1H, dd, J=17, 6.6Hz), 3.34 (9H, s), 3.80 to 4.05 (4H, m), 5.60 to 5.70 (1H, m)

MS (ESI) m/z: 442 [(MH-HNO$_3$)$^+$]

EXAMPLE 83 m.p.: 62° to 64° C.

IR (Nujol) cm$^{-1}$: 1740

NMR (CDCl$_3$) δ: 0.88 (3H, t, J=6.9Hz), 0.89 (3H, t, J=6.8 Hz), 1.26 to 1.34 (24H, m), 1.56 to 1.66 (4H, m), 2.34 (2H, t, J=7.6Hz), 2.76 (1H, dd, J=14, 5.7Hz), 2.81 (1H, dd, J=14, 6.7Hz), 3.34 (9H, s), 3.93 to 4.13 (4H, m), 5.62 to 5.69 (1H, m)

MS (ESI) m/z: 442 [(MH-HNO$_3$)$^+$]

EXAMPLE 84

Resinous product

IR (Neat) cm$^{-1}$: 2920, 2840, 1740

NMR (CDCl$_3$) δ: 0.88 (3H, t, J=6.8Hz), 1.24 to 1.30 (19H, m), 1.55 to 1.65 (2H, m), 1.96 (2H, quint, J=6.8Hz), 2.32 to 2.41 (4H, m), 2.76 (1H, dd, J=17, 5.7Hz), 2.81 (1H, dd, J=17, 6.7Hz), 3.34 (9H, s), 3.92 to 4.17 (6H, m), 5.62 to 5.69 (1H, m)

MS (ESI) m/z: 458 [(MH-HNO$_3$)$^+$]

EXAMPLE 85

Resinous product

IR (Neat) cm$^{-1}$: 3380 (br), 2920, 2840, 1740

NMR (CDCl$_3$) δ: 0.89 (3H, t, J=6.8Hz), 1.28 (22H, br), 1.56 to 1.65 (6H, m), 1.85 (1H, br), 2.35 (2H, t, J=7.6Hz), 2.76 (1H, dd, J=17, 5.7Hz), 2.81 (1H, dd, J=17, 6.7Hz), 3.33 (9H, s), 3.63 (2H, t, J=6.6Hz), 3.92 to 4.13 (4H, m), 5.62 to 5.69 (1H, m)

MS (ESI) m/z: 458 [(MH-HNO$_3$)$^+$]

EXAMPLE 86 m.p.: 87° to 88° C.

IR (Nujol) cm$^{-1}$: 1740

NMR (CDCl$_3$) δ: 0.88 (3H, t, J=6.7Hz), 1.25 (3H, t, J=7.1 Hz), 1.26 to 1.33 (20H, m), 1.56 to 1.65 (2H, m), 2.49 to 2.88 (6H, m), 3.36 (9H, s), 3.97 to 4.11 (4H, m), 4.11 (2H, q, J=7.1Hz), 5.65 to 5.73 (1H, m)

MS (ESI) m/z: 472 [(MH-HNO$_3$)$^+$]

EXAMPLE 87 m.p.: 46° to 48° C.

IR (Nujol) cm$^{-1}$: 1740

NMR (CDCl$_3$) δ: 0.88 (6H, t, J=6.8Hz), 1.26 (24H, br s), 1.55 to 1.65 (4H, m), 2.34 (2H, t, J=7.6Hz), 2.75 (1H, dd, J=17, 5.8Hz), 2.81 (1H, dd, J=17, 6.7Hz), 3.32 (9H, s), 3.90 to 4.13 (4H, m), 5.61 to 5.69 (1H, m)

MS (ESI) m/z: 442 [(MH-HNO$_3$)$^+$]

EXAMPLE 88 m.p.: 55° to 57° C.

IR (Nujol) cm$^{-1}$: 1740

NMR (CDCl$_3$) δ: 0.88 (6H, t, J=6.6Hz), 1.26 (28H, br s), 1.55 to 1.65 (4H, m), 2.34 (2H, t, J=7.6Hz), 2.76 (1H, dd, J=17, 5.8Hz), 2.81 (1H, dd, J=17, 6.7Hz), 3.34 (9H, s), 3.93 to 4.13 (4H, m), 5.61 to 5.69 (1H, m)

MS (ESI) m/z: 470 [(MH-HNO$_3$)$^+$]

EXAMPLE 89 m.p.: 62° to 64° C.

IR (Nujol) cm$^{-1}$: 1740

NMR (CDCl$_3$) δ: 0.88 (6H, t, J=6.6Hz), 1.26 (32H, br s), 1.55 to 1.66 (4H, m), 2.34 (2H, t, J=7.6Hz), 2.76 (1H, dd, J=17, 5.7Hz), 2.81 (1H, dd, J=17, 6.6Hz), 3.34 (9H, s), 3.93 to 4.13 (4H, m), 5.62 to 5.69 (1H, m)

MS (ESI) m/z: 498 [(MH-HNO$_3$)$^+$]

EXAMPLE 90 m.p.: 79° to 81° C.

IR (Nujol) cm$^{-1}$: 1740

NMR (CDCl$_3$) δ: 0.88 (3H, t, J=6.7Hz), 1.25 (3H, t, J=7.1 Hz), 1.26 to 1.33 (16H, m), 1.56 to 1.66 (2H, m), 2.49 to 2.87 (6H, m), 3.36 (9H, s), 3.97 to 4.11 (4H, m), 4.12 (2H, q, J=7.1Hz), 5.65 to 5.73 (1H, m) MS (ESI) m/z: 444 [(MH-HNO$_3$)$^+$]

EXAMPLE 91 m.p.: 81° to 82° C.

IR (Nujol) cm$^{-1}$: 1740

NMR (CDCl$_3$) δ: 0.88 (3H, t, J=6.8Hz), 1.25 (3H, t, J=7.1 Hz), 1.26 to 1.33 (18H, m), 1.56 to 1.65 (2H, m), 2.49 to 2.87 (6H, m), 3.36 (9H, s), 3.97 to 4.11 (4H, m), 4.12 (2H, q, J=7.1Hz), 5.65 to 5.73 (1H, m)

MS (ESI) m/z: 458 [(MH-HNO$_3$)$^+$]

EXAMPLE 92 m.p.: 85° to 86° C.

IR (Nujol) cm$^{-1}$: 1740

NMR (CDCl$_3$) δ: 0.88 (3H, t, J=6.8Hz), 1.25 (3H, t, J=7.1 Hz), 1.26 to 1.33 (22H, m), 1.56 to 1.66 (2H, m), 2.49 to 2.88 (6H, m), 3.36 (9H, s), 3.97 to 4.11 (4H, m), 4.12 (2H, q, J=7.1Hz), 5.65 to 5.73 (1H, m)

MS (ESI) m/z: 486 [(MH-HNO$_3$)$^+$]

REFERENCE EXAMPLE 1

After a mixture of n-pentadecanoic acid (25 g, 103 mmol) and thionyl chloride (3.15 g, 26.5 mmol) was stirred for 3 hours at 75° to 80° C., a solution of L-carnitine (4.27 g, 26.5 mmol) in 25 g of trichloroacetic acid was added at 60° C. The resulting mixture was stirred for 3 hours at 80° C. under argon atmosphere and then poured into stirred 100 ml of diethyl ether. The precipitates were collected by filtration, washed with diethyl ether and then dried to give 11.8 g of a crude desired product as a colorless solid. 11.8 g of the crude product was recrystallized from isopropanol to provide 9.38 g of (R)-(3-carboxy-2-pentadecanoyloxypropyl) trimethylammonium chloride as colorless needles.

m.p.: 167° to 169° C.

IR (Nujol) cm$^{-1}$: 3020 to 2480, 1740, 1710

NMR (DMSO-d$_6$) δ: 0.85 (3H, t, J=6.7Hz), 1.24 (22H, br s), 1.47 to 1.57 (2H, m), 2.23 to 2.40 (2H, m), 2.62 to 2.76 (2H, m), 3.12 (9H, s), 3.68 (1H, br d), 3.81 (1H, dd, J=14, 8.1Hz), 5.42 to 5.49 (1H, m)

REFERENCE EXAMPLES 2 to 14

By processing corresponding starting compounds in the same manner as described in Reference example 1, the compounds shown in the following Table 9 were obtained.

TABLE 9

$$\begin{array}{c} CH_2COOH \\ | \\ CHOR^4 \\ | \\ CH_2-N^+(CH_3)_3 \end{array} \quad X^-$$

| Reference example No. | $R^4$ | $X^-$ | Physical properties |
|---|---|---|---|
| 2 | $-CO(CH_2)_{11}CH_3$ | $Cl^-$ | m.p.: 161 to 163° C. IR(Nujol)cm$^{-1}$: 3020 to 2480, 1740, 1710 NMR(DMSO-d$_6$)δ: 0.86(3H, t, J=6.8Hz), 1.24(18H, br s), 1.47 to 1.57(2H, m), 2.23 to 2.40(2H, m), 2.63 to 2.77 (2H, m), 3.12(9H, s), 3.69 (1H, br d), 3.83(1H, dd, J=14, 8.4Hz), 5.42 to 5.49 (1H, m) |
| 3 | $-CO(CH_2)_{15}CH_3$ | $Cl^-$ | m.p.: 165 to 167° C. IR(Nujol)cm$^{-1}$: 3020 to 2480, 1740, 1710 NMR(DMSO-d$_6$)δ: 0.85(3H, t, J=6.8Hz), 1.23(26H, br s), 1.47 to 1.57(2H, m), 2.23 to 2.40(2H, m), 2.62 to 2.76 (2H, m), 3.11(9H, s), 3.67 (1H, br d), 3.81(1H, dd, J=14, 8.3Hz), 5.41 to 5.49 (1H, m) |
| 4 | $-CO(CH_2)_{14}CH_3$ | $Cl^-$ | m.p.: 168 to 170° C. IR(Nujol)cm$^{-1}$: 3020 to 2480, 1740, 1710 NMR(DMSO-d$_6$)δ: 0.86(3H, t, J=6.7Hz), 1.24(24H, br s), 1.47 to 1.57(2H, m), 2.23 to 2.40(2H, m), 2.62 to 2.76 (2H, m), 3.12(9H, s), 3.68 (1H, br d), 3.81(1H, dd, J=14, 8.2Hz), 5.42 to 5.49 (1H, m) |
| 5 | $-CO(CH_2)_9CH_3$ | $Cl^-$ | m.p.: 172 to 173° C. IR(Nujol)cm$^{-1}$: 3400, 1740, 1700 NMR(DMSO-d$_6$)δ: 0.86(3H, t, J=6.6Hz), 1.24(14H, s), 1.45 to 1.55(2H, m), 2.30 to 2.35 (2H, m), 2.65 to 2.70(2H, m), 3.31(9H, s), 3.65(1H, d, J=14Hz), 3.82(1H, dd, J=14, 8.2Hz), 5.40 to 5.50 (1H, m) |
| 6 | $-CO(CH_2)_5CH_3$ | $Cl^-$ | m.p. : 168 to 169° C. IR(Nujol)cm$^{-1}$: 3400, 1740, 1700 NMR(DMSO-d$_6$)δ: 0.86(3H, t, J=6.9Hz), 1.25(6H, br s), 1.50 to 1.55(2H, m), 2.32 (2H, t, J=7.4Hz), 2.70(2H, d, J=6.4Hz), 3.12(9H, s), 3.67(1H, d, J=13Hz), 3.82 (1H, dd, J=14, 8.2Hz), 5.40 to 5.50(1H, m) |
| 7 | $-COCH_2CH_3$ | $Cl^-$ | m.p.: 174 to 176° C. IR(Nujol)cm$^{-1}$: 3400, 1720 NMR(DMSO-d$_6$)δ: 1.04(3H, t, J=7.5Hz), 2.52 to 2.40(2H, m), 2.70(2H, d, J=6.2Hz), 3.12(9H, s), 3.67(1H, d, |

TABLE 9-continued $$\begin{array}{c} CH_2COOH \\ | \\ CHOR^4 \\ | \\ CH_2-N^+ \begin{array}{c} CH_3 \\ CH_3 \\ CH_3 \end{array} \quad X^- \end{array}$$

| Reference example No. | R⁴ | X⁻ | Physical properties |
|---|---|---|---|
| 8 | —CO(CH₂)₃CH₃ | Cl⁻ | J=14Hz), 3.83(1H, dd, J=14, 8.4Hz), 5.40 to 5.50(1H, m) m.p.: 147 to 150° C. IR(Nujol)cm⁻¹: 3400, 1735 NMR(DMSO-d₆)δ: 0.87(3H, t, J=7.4Hz), 1.23 to 1.36(2H, m), 1.47 to 1.57(2H, m), 2.24 to 2.41(2H, m), 2.62 to 2.76(2H, m), 3.13(9H, s), 3.70(1H, br d), 3.82(1H, dd, J=14, 8.1Hz), 5.42 to 5.49(1H, m) |
| 9 | —CO(CH₂)₂CH(CH₃)₂ | Cl⁻ | m.p.: 146 to 148° C. IR(Nujol)cm⁻¹: 3400, 1740 NMR(DMSO-d₆)δ: 0.86(6H, d, J=6.5Hz), 1.40 to 1.60(3H, m), 2.25 to 2.40(2H, m), 2.70(2H, d, J=5.4Hz), 3.12 (9H, s), 3.69(1H, d, J=13 Hz), 3.83(1H, dd, J=14, 8.3 Hz), 5.40 to 5.50(1H, m), 12.75(1H, br s) |
| 10 | —CO(CH₂)₇CH₃ | Cl⁻ | m.p.: 171 to 171.5° C. IR(Nujol)cm⁻¹: 3400, 1740 NMR(DMSO-d₆)δ: 0.86(3H, t, J=6.6Hz), 1.25(10H, s), 1.50 to 1.60(2H, m), 2.24 to 2.28 (2H, m), 2.69(2H, d, J=6.3 Hz), 3.12(9H, s), 3.67(1H, d, J=14Hz), 3.82(1H, dd, J= 14, 8.3Hz), 5.40 to 5.50(1H, m), 12.74(1H, br d) |
| 11 | —CO(CH₂)₁₂CH₃ | Cl⁻ | m.p.: 171 to 173° C. IR(Nujol)cm⁻¹: 1740 NMR(DMSO-d₆)δ: 0.86(3H, t, J=6.9Hz), 1.24(20H, s), 1.50 to 1.60(2H, m), 2.20 to 2.70 (2H, m), 2.70(2H, d, J=6.2 Hz), 3.12(9H, s), 3.68(1H, d, J=13Hz), 3.82(1H, dd, J=14, 8.1 Hz), 5.40 to 5.50 (1H, m) |
| 12 | —CO(CH₂)₄CH₃ | Cl⁻ | m.p.: 173 to 174° C. IR(Nujol)cm⁻¹: 1740, 1700 NMR(DMSO-d₆)δ: 0.86(3H, t, J=6.9Hz), 1.20 to 1.35(4H, m), 1.45 to 1.60(2H, m), 2.25 to 2.40(2H, m), 2.70 (2H, d, J=5.8Hz), 3.12(9H, s), 3.67(1H, d, J=13Hz), 3.82(1H, dd, J=14, 8.2Hz), 5.40 to 5.50(1H, m), 12.75 (1H, br s) |
| 13 | —COCH(CH₃)₂ | Cl⁻ | m.p.: 166 to 167° C. IR(Nujol)cm⁻¹: 1720, 1700 NMR(DMSO-d₆)δ: 1.08(3H, s), 1.11(3H, s), 2.50 to 2.80(3H, m), 3.12(9H, s), 3.69(1H, d, J=14Hz), 3.84 (1H, dd, J=14, 8.2Hz), 5.40 to 5.50(1H, m), 12.76(1H, br s) |

TABLE 9-continued

CH₂COOH
|
CHOR⁴           CH₃      X⁻
|              /
CH₂—N⁺—CH₃
               \
                CH₃

| Reference example No. | R⁴ | X⁻ | Physical properties |
|---|---|---|---|
| 14 | —COCH(CH₂CH₂CH₃)₂ | Cl⁻ | m.p.: 182 to 184° C. IR(Nujol)cm⁻¹: 1720 NMR(DMSO-d₆)δ: 0.85(6H, t, J=7.2Hz), 1.15 to 1.60(8H, m), 2.30 to 2.40(1H, m), 2.69(1H, dd, J=17, 4.8Hz), 2.77(1H, dd, J=17, 6.4Hz), 3.13(9H, s), 3.74(1H, d, J=14Hz), 3.86(1H, dd, J=15, 7.7Hz), 5.40 to 5.50(1H, m), 12.80(1H, br s) |

REFERENCE EXAMPLE 15

L-Carnitine (2.0 g, 12.4 mmol) was dissolved in 3 ml of trifluoroacetic acid under heating (at 60° C.), and 8 ml (37.2 mmol) of 10-undecenoyl chloride was added to the solution. The vessel was closed tightly, and the mixture was vigorously shaken by hands for 5 minutes at the same temperature until the mixture became homogeneous. The homogeneous solution was further stirred for 10 minutes at the same temperature. After the solvent of the reaction mixture was removed, the residue was dissolved in 100 ml of petroleum ether, the solution was poured into 100 ml of ice water, and the mixture was stirred for 30 minutes at room temperature. Subsequently, the mixture was washed with a solution of 100 ml of ethanol and 100 ml of ether. The aqueous layer was further washed twice with a mixture of 60 ml of ethanol and 60 ml of ether. The separated aqueous layer was extracted with 120 ml of n-butanol after addition of a suitable amount of water. The n-butanol layer was successively washed with 40 ml of water, 40 ml of a phosphate buffer (67 mmol, pH 7.2) and then 40 ml of water. The solvent was removed, and the residue was azeotroped with toluene and ethyl acetate and recrystallized from ethyl acetate to give 1.81 g of (R)-[3-carboxy-2-(10-undecenoyloxypropyl)]trimethylammonium chloride as colorless crystals.

m.p.: 154° to 156° C.

IR (Nujol) cm⁻¹: 1740

NMR (DMSO-d₆) δ: 1.20 to 1.40 (10H, m), 1.45 to 1.60 (2H, m), 1.95 to 2.05 (2H, m), 2.25 to 2.35 (2H, m), 2.65 (2H, d, J=6.1Hz), 3.11 (9H, s), 3.66 (1H, d, J=13Hz), 3.81 (1H, dd, J=14, 8.3Hz), 4.90 to 5.05 (2H, m), 5.40 to 5.50 (1H, m), 5.70 to 5.90 (1H, m)

REFERENCE EXAMPLE 16

By processing L-carnitine and linoleoyl chloride in the same manner as described in Reference example 15, (R)-(3-carboxy-2-linoleoyloxypropyl)trimethylammonium chloride was obtained.

IR (Neat) cm⁻¹: 1740

NMR (DMSO-d₆) δ: 0.86 (3H, t, J=6.7Hz), 1.20 to 1.40 (14H, m), 1.45 to 1.60 (2H, m), 1.95 to 2.05 (4H, m), 2.25 to 2.35 (2H, m), 2.68 (2H, d, J=5.9Hz), 2.74 (2H, t, J=5.5Hz), 3.10 (9H, s), 3.62 (1H, d, J=13Hz), 3.81 (1H, dd, J=15, 8.3Hz), 5.25 to 5.40 (4H, m), 5.40 to 5.50 (1H, m)

REFERENCE EXAMPLE 17

The same procedure as described in Reference example 1 was carried out to give the following compound.

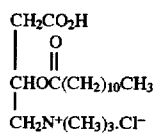

m.p.: 174° to 176° C.

IR (Nujol) cm⁻¹: 1735, 1705

NMR (DMSO-d₆) δ: 0.86 (3H, t, J=6.8Hz), 1.24 (16H, br s), 1.48 to 1.57 (2H, m), 2.24 to 2.40 (2H, m), 2.63 to 2.77 (2H, m), 3.12 (9H, s), 3.69 (1H, br d), 3.82 (1H, dd, J=14, 8.2Hz), 5.43 to 5.49 (1H, m)

MS (ESI) m/z: 366 [(MNa-HCl)⁺], 344 [(MH-HCl)⁺]

REFERENCE EXAMPLE 18

The same procedure as described in Reference example 1 was carried out to give the following compound.

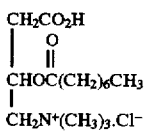

m.p.: 176° to 177° C.

IR (Nujol) cm⁻¹: 1735, 1705

NMR (DMSO-d₆) δ: 0.86 (3H, t, J=6.7Hz), 1.25 (8H, br s), 1.48 to 1.58 (2H, m), 2.24 to 2.40 (2H, m), 2.63 to 2.77 (2H, m), 3.13 (9H, s), 3.70 (1H, br d), 3.82 (1H, dd, J=14, 8.1Hz), 5.42 to 5.49 (1H, m), 12.8 (1H, br)

MS (ESI) m/z: 288 [(MH-HCl)⁺]

REFERENCE EXAMPLE 18

A mixture of ethyl succinyl chloride (17.6 g, 107 mmol) and water (1.28 g, 71.0 mmol) was stirred for 1.5 hours at 60° to 70° C. and then a solution of L-carnitine (3.83 g, 23.8 mmol) in 12 g of trichloroacetic acid at 40° C. was added. The mixture was stirred for 21.5 hours at 60° to 70° C. and cooled to room temperature. After 200 ml of diethyl ether was added to the mixture, the resulting oily material was washed twice with 200 ml of diethyl ether by decantation. The oily residue was solidified by the addition of 150 ml of tetrahydrofuran. The resulting solid was triturated, collected by filtration, washed with tetrahydrofuran and dried to give 6.5 g of (R)-[[3-carboxy-2-(3-ethoxycarbonyl)propionyloxy]propyl]trimethylammonium chloride as a colorless solid.

m.p.: 97° to 99° C.

IR (Nujol) cm$^{-1}$: 3400 (br), 1730

NMR (DMSO-d$_6$) δ: 1.18 (3H, t, J=7.1Hz), 2.54 to 2.64 (4H, m), 2.68 to 2.71 (2H, m), 3.13 (9H, s), 3.69 (1H, br d), 3.85 (1H, dd, J=14, 8.6Hz), 4.06 (2H, q, J=7.1Hz), 5.44 to 5.51 (1H, m), 12.8 (1H, br)

MS (ESI) m/z: 290 [(MH-HCl)$^+$]

The carnitine derivative (I) according to the present invention has an excellent hair-growing action.

Further, the carnitine derivative (I) according to the present invention has low toxicity and high safety. For example, when an ethanol solution containing 2% of (R)-(2-tridecanoyloxy-3-tridecyloxycarbonylpropyl)trimethylammonium chloride which is the active ingredient of the present invention was applied for 30 days, abnormality of skin was not observed.

Thus, the carnitine derivative (I) according to the present invention is useful as a hair-growing (restoration) agent and can be effectively used for promotion of hair growth in human beings or animals such as sheep or goat which supply woolen goods such as wool or cashmere. Moreover, the carnitine derivative (I) can be effectively used for prophylaxis and treatment of male pattern alopecia, alopecia senilis, telogen effluvium and canities.

We claim:

1. A method for promotion of hair growth in a human or an animal in need thereof, which comprises applying to the skin of said human or animal an agent which comprises a carnitine compound represented by the formula (I):

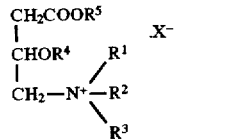

wherein R$^1$ to R$^3$ each represent a methyl group; R$^4$ represents an aliphatic acyl group having 3 to 18 carbon atoms which may be substituted; R$^5$ represents an alkyl group having 3 to 21 carbon atoms which may be substituted, or an alkenyl group having 3 to 21 carbon atoms which may be substituted; and X$^-$ represents an anion of a pharmaceutically acceptable acid, and wherein said carnitine compound is an active ingredient of said agent which is present in an amount sufficient to promote hair growth in a human or an animal.

2. The method according to claim 1, wherein each of the R$^1$ to R$^3$ is a methyl group; R$^4$ is an aliphatic acyl group having 3 to 18 carbon atoms which may have a substituent selected from the group consisting of hydroxy group and an alkoxycarbonyl group having 2 to 7 carbon atoms; and R$^5$ is an alkyl group having 3 to 21 carbon atoms which may have a substituent selected from the group consisting of hydroxy group and an alkoxycarbonyl group having 2 to 7 carbon atoms, or an alkenyl group having 3 to 21 carbon atoms which may have a substituent selected from the group consisting of hydroxy group and an alkoxycarbonyl group having 2 to 7 carbon atoms.

3. The method according to claim 1, wherein each of R$^1$ to R$^3$ is a methyl group; R$^4$ is an aliphatic acyl group having 3 to 18 carbon atoms; and R$^5$ is an alkyl group having 3 to 21 carbon atoms, or an alkenyl group having 3 to 21 carbon atoms.

4. The method according to claim 3, wherein:

each of R$^1$ to R$^3$ is methyl group;

R$^4$ is a propionyl group, butyryl group, isobutyryl group, crotonoyl group, methacryloyl group, valeryl group, isovaleryl group, pivaloyl group, hexanoyl group, 4-methylvaleryl group, sorbinoyl group, heptanoyl group, octanoyl group, 2-propylvaleryl group, nonanoyl group, decanoyl group, undecanoyl group, tetradecanoyl group, dodecanoyl group, tridecanoyl group, 10-undecenoyl group, pentadecanoyl group, hexadecanoyl group, heptadecanoyl group, octadecanoyl group, oleoyl group, elaidoyl group, linoleoyl group, or linolenoyl group;

R$^5$ is a propyl group, isopropyl group, butyl group, isobutyl group, 1-methylpropyl group, 1,1-dimethylethyl group, pentyl group, 1-methylbutyl group, 2-methylbutyl group, 3-methylbutyl group, 1,1-dimethylpropyl group, 1,2-dimethylpropyl group, 2,2-dimethylpropyl group, 1-ethylpropyl group, 2-ethylpropyl group, hexyl group, isohexyl group, 1-methylpentyl group, 2-methylpentyl group, 3-methylpentyl group, 1-ethylbutyl group, 2-ethylbutyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1-ethyl-1-methylpropyl group, 1-ethyl-2-methylpropyl group, 2-ethyl-1-methylpropyl group, 2-ethyl-2-methylpropyl group, 1-methyl-2-ethylpropyl group, 1,1,2-timethylpropyl group, 1,2,2-trimethylproyl group, heptyl group, octyl group, 2-propylpentyl group, nonyl group, decyl group, undecyl group, dodecyl group, tridecyl group, tetradecyl group, pentadecyl group, hexadecyl group, heptadecyl group, octadecyl group, nonadecyl group, isosyl group, or heneicosyl group; and X$^-$ is an anion of a pharmaceutically acceptable acid selected from the group consisting of chloride, acetate, citrate, nicotinate, nitrate, sulfonate and salicylate.

5. The method according to claim 3, wherein:

each of R$^1$ to R$^3$ is a methyl group;

R$^4$ is a propionyl group, isobutyryl group, valeryl group, hexanoyl group, 4-methylvaleryl group, heptanoyl group, 2-propylvaleryl group, nonanoyl group, undecanoyl group, 10-undecenoyl group, tridecanoyl group, tetradecanoyl group, pentadecanoyl group, hexadecanoyl group, heptadecanoyl group, or linoleoyl group; and R$^5$ is propyl group, pentyl group, 2-methylbutyl group, isohexyl group, heptyl group, nonyl group, decyl group, undecyl group, dodecyl group, tridecyl group, tetradecyl group, pentadecyl group, heneicosyl group or 10-undecenyl group.

6. The method according to claim 1, wherein each of R$^1$ to R$^3$ is a methyl group, R$^4$ is an aliphatic acyl group having 3 to 15 carbon atoms, and R$^5$ is an alkyl group having 3 to 15 carbon atoms or an alkenyl group having 3 to 15 carbon atoms.

7. The method according to claim 6, wherein:

each of R$^1$ to R$^3$ is a methyl group;

R$^4$ is propionyl group, isobutyryl group, valeryl group, 4-methylvaleryl group, hexanoyl group, heptanoyl group, undecanoyl group, 10-undecenoyl group, tridecanoyl group or pentadecanoyl group; and $R^5$ is propyl group, petnyl group, 2-methylbutyl group, heptyl group, nonyl group, undecyl group, dodecyl group, tridecyl group, tetradecyl group or pentadecyl group.

8. The method according to claim 1, wherein each of $R^1$ to $R^3$ is a methyl group; $R^4$ is an aliphatic acyl group having 4 to 18 carbon atoms; and $R^5$ is an alkyl group having 11 to 21 carbon atoms.

9. The method according to claim 1, wherein the sum of the carbon number of the aliphatic acyl moiety of $R^4$ and the carbon number of the alkyl moeity or the alkenyl moiety of $R^5$ is 6 to 34.

10. The method according to claim 3, wherein the sum of the carbon number of $R^4$ and the carbon number of $R^5$ is 6 to 34.

11. The method according to claim 10, wherein the combination of the carbon number of $R^4$ and the carbon number of $R^5$ is selected from the group consisting of:

(1) in the case of the sum of the carbon numbers being 6, a combination wherein the carbon number of $R^4$ is 3 and the carbon number of $R^5$ is 3;

(2) in the case of the sum of the carbon numbers being 8, a combination wherein the carbon number of $R^4$ is 5 and the carbon number of $R^5$ is 3;

(3) in the case of the sum of the carbon numbers being 12, a combination wherein the carbon number of $R^4$ is 5 and the carbon number of $R^5$ is 7;

(4) in the case of the sum of the carbon numbers being 14, a combination wherein the carbon number of $R^4$ is 3 and the carbon number of $R^5$ is 11, or the carbon number of $R^4$ is 11 and the carbon number of $R^5$ is 3;

(5) in the case of the sum of the carbon numbers being 15, a combination wherein the carbon number of $R^4$ is 4 and the carbon number of $R^5$ is 11;

(6) in the case of the sum of the carbon numbers being 16, a combination wherein the carbon number of $R^4$ is 3 and the carbon number of $R^5$ is 13, or the carbon number of $R^4$ is 5 and the carbon number of $R^5$ is 11, or the carbon number of $R^4$ is 7 and the carbon number of $R^5$ is 9, or the carbon number of $R^4$ is 11 and the carbon number of $R^5$ is 5, or the carbon number of $R^4$ is 13 and the carbon number of $R^5$ is 3;

(7) in the case of the sum of the carbon numbers being 17, a combination wherein the carbon number of $R^4$ is 4 and the carbon number of $R^5$ is 13, or the carbon number of $R^4$ is 5 and the carbon number of $R^5$ is 12, or the carbon number of $R^4$ is 6 and the carbon number of $R^5$ is 11;

(8) in the case of the sum of the carbon numbers being 18, a combination wherein the carbon number of $R^4$ is 3 and the carbon number of $R^5$ is 15, or the carbon number of $R^4$ is 4 and the carbon number of $R^5$ is 14, or the carbon number of $R^4$ is 5 and the carbon number of $R^5$ is 13, or the carbon number of $R^4$ is 6 and the carbon number of $R^5$ is 12, or the carbon number of $R^4$ is 7 and the carbon number of $R^5$ is 11, or the carbon number of $R^4$ is 9 and the carbon number of $R^5$ is 9, or the carbon number of $R^4$ is 11 and the carbon number of $R^5$ is 7, or the carbon number of $R^4$ is 13 and the carbon number of $R^5$ is 5, or the carbon number of $R^4$ is 15 and the carbon number of $R^5$ is 3;

(9) in the case of the sum of the carbon numbers being 19, a combination wherein the carbon number of $R^4$ is 4 and the carbon number of $R^5$ is 15, or the carbon number of $R^4$ is 6 and the carbon number of $R^5$ is 13, or the carbon number of $R^4$ is 8 and the carbon number of $R^5$ is 11, or the carbon number of $R^4$ is 11 and the carbon number of $R^5$ is 8, or the carbon number of $R^4$ is 13 and the carbon number of $R^5$ is 6, or the carbon number of $R^4$ is 15 and the carbon number of $R^5$ is 4, or the carbon number of $R^4$ is 16 and the carbon number of $R^5$ is 3;

(10) in the case of the sum of the carbon numbers being 20, a combination wherein the carbon number of $R^4$ is 5 and the carbon number of $R^5$ is 15, or the carbon number of $R^4$ is 7 and the carbon number of $R^5$ is 13, or the carbon number of $R^4$ is 9 and the carbon number of $R^5$ is 11, or the carbon number of $R^4$ is 11 and the carbon number of $R^5$ is 9, or the carbon number of $R^4$ is 13 and the carbon number of $R^5$ is 7;

(11) in the case of the sum of the carbon numbers being 21, a combination wherein the carbon number of $R^4$ is 8 and the carbon number of $R^5$ is 13, or the carbon number of $R^4$ is 16 and the carbon number of $R^5$ is 5, or the carbon number of $R^4$ is 18 and the carbon number of $R^5$ is 3;

(12) in the case of the sum of the carbon numbers being 22, a combination wherein the carbon number of $R^4$ is 11 and the carbon number of $R^5$ is 11, or the carbon number of $R^4$ is 7 and the carbon number of $R^5$ is 15, or the carbon number of $R^4$ is 13 and the carbon number of $R^5$ is 9;

(13) in the case of the sum of the carbon numbers being 23, a combination wherein the carbon number of $R^4$ is 8 and the carbon number of $R^5$ is 15;

(14) in the case of the sum of the carbon numbers being 25, a combination wherein the carbon number of $R^4$ is 13 and the carbon number of $R^5$ is 12, or the carbon number of $R^4$ is 14 and the carbon number of $R^5$ is 11, or the carbon number of $R^4$ is 16 and the carbon number of $R^5$ is 9;

(15) in the case of the sum of the carbon numbers being 26, a combination wherein the carbon number of $R^4$ is 13 and the carbon number of $R^5$ is 13, or the carbon number of $R^4$ is 15 and the carbon number of $R^5$ is 11;

(16) in the case of the sum of the carbon numbers being 27, a combination wherein the carbon number of $R^4$ is 16 and the carbon number of $R^5$ is 11;

(17) in the case of the sum of the carbon numbers being 28, a combination wherein the carbon number of $R^4$ is 15 and the carbon number of $R^5$ is 13, or the carbon number of $R^4$ 17 and the carbon number of $R^5$ is 11, or the carbon number of R4 is 16 and the carbon number of $R^5$ is 12;

(18) in the case of the sum of the carbon numbers being 30, a combination wherein the carbon number of $R^4$ is 15 and the carbon number of $R^5$ is 15; and

(19) in the case of the sum of the carbon numbers being 34, a combination wherein the carbon number of $R^4$ is 13 and the carbon number of $R^5$ is 21.

12. The method according to claim 11, wherein the sum of the carbon number of $R^4$ and the carbon number of $R^5$ is 14 to 26.

13. The method according to claim 5 wherein $R^1$ to $R^3$ each represent a methyl group;

$R^4$ and $R^5$ represent a combination selected from the group consisting of:

$R^4$ is pentadecanoyl group and $R^5$ is undecyl group;

$R^4$ is valeryl group and $R^5$ is tridecyl group;
$R^4$ is propionyl group and $R^5$ is undecyl group;
$R^4$ is tridecanoyl group and $R^5$ is pentyl group;
$R^4$ is heptanoyl group and $R^5$ is nonyl group;
$R^4$ is undecanoyl group and $R^5$ is pentyl group;
$R^4$ is valeryl group and $R^5$ is undecyl group;
$R^4$ is undecanoyl group and $R^5$ is heptyl group;
$R^4$ is tridecanoyl group and $R^5$ is heptyl group;
$R^4$ is isobutyryl group and $R^5$ is tridecyl group;
$R^4$ is propionyl group and $R^5$ is tridecyl group;
$R^4$ is 4-methylvaleryl group and $R^5$ is dodecyl group;
$R^4$ is 4-methylvaleryl group and $R^5$ is tridecyl group;
$R^4$ is isobutyryl group and $R^5$ is tetradecyl group;
$R^4$ is valeryl group and $R^5$ is pentadecyl group;
$R^4$ is propionol group and $R^5$ is pentadecyl group; and
$R^4$ is hexanoyl group and $R^5$ is undecyl group;
and $X^-$ represents an anion of a pharmaceutically acceptable acid.

14. The method according to claim 13, wherein the anion of a pharmaceutically acceptable acid is an anion selected from the group consisting of chloride, acetate, citrate, nicotinate, nitrate, sulfonate and salicylate.

15. The method according to claim 1, wherein $R^1$ to $R^3$ each represent a methyl group, $R^4$ is a tridecanoyl group, and $R^5$ is a heptyl group.

16. A method for prophylaxis or treatment of male pattern alopecia, alopecia senilis, telogen effluvium and canities in humans, which comprises applying to the skin of a human subject in need thereof an agent comprising a carnitine compound represented by the formula (I):

wherein $R^1$ to $R^3$ each represent a methyl group; $R^4$ represents an aliphatic acyl group having 3 to 18 carbon atoms which may be substituted; $R^5$ represents an alkyl group having 3 to 21 carbon atoms which may be substituted, or an alkenyl group having 3 to 21 carbon atoms which may be substituted; and $X^-$ represents an anion of a pharmaceutically acceptable acid, and wherein said carnitine compound is an active ingredient of said agent which is present in an amount sufficient for prophylaxis or treatment of male pattern alopecia, alopecia senilis, telogen effluvium and canities in humans.

17. The method according to claim 16, wherein each of the $R^1$ to $R^3$ is a methyl group; $R^4$ is an aliphatic acyl group having 3 to 18 carbon atoms which may have a substituent selected from the group consisting of hydroxy group and an alkoxycarbonyl group having 2 to 7 carbon atoms; and $R^5$ is an alkyl group having 3 to 21 carbon atoms which may have a substituent selected from the group consisting of hydroxy group and an alkoxycarbonyl group having 2 to 7 carbon atoms, or an alkenyl group having 3 to 21 carbon atoms which may have a substituent selected from the group consisting of hydroxy group and an alkoxycarbonyl group having 2 to 7 carbon atoms.

18. The method according to claim 16, wherein each of $R^1$ to $R^3$ is a methyl group; $R^4$ is an aliphatic acyl group having 3 to 18 carbon atoms; and $R^5$ is an alkyl group having 3 to 21 carbon atoms, or an alkenyl group having 3 to 21 carbon atoms.

19. The method according to claim 18, wherein:

each of $R^1$ to $R^3$ is methyl group;

$R^4$ is a propionyl group, butyryl group, isobutyryl group, crotonoyl group, methacryloyl group, valeryl group, isovaleryl group, pivaloyl group, hexanoyl group, 4-methylvaleryl group, sorbinoyl group, heptanoyl group, octanoyl group, 2-propylvaleryl group, nonanoyl group, decanoyl group, undecanoyl group, 10-undecenoyl group, dodecanoyl group, tridecanoyl group, tetradecanoyl group, pentadecanoyl group, hexadecanoyl group, heptadecanoyl group, octadecanoyl group, oleoyl group, elaidoyl group, linoleoyl group, or linolenoyl group;

$R^5$ is a propyl group, isopropyl group, butyl group, isobutyl group, 1-methylpropyl group, 1,1-dimethylethyl group, pentyl group, 1-methylbutyl group, 2-methylbutyl group, 3-methylbutyl group, 1,1-dimethylpropyl group, 1,2-dimethylpropyl group, 2,2-dimethylpropyl group, 1-ethylpropyl group, 2-ethylpropyl group, hexyl group, isohexyl group, 1-methylpentyl group, 2-methylpentyl group, 3-methylpentyl group, 1-ethylbutyl group, 2-ethylbutyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1-ethyl-1-methylpropyl group, 1-ethyl-2-methylpropyl group, 2-ethyl-1-methylpropyl group, 2-ethyl-2-methylpropyl group, 1-methyl-2-ethylpropyl group, 1,1,2-timethylpropyl group, 1,2,2-trimethylproyl group, heptyl group, octyl group, 2-propylpentyl group, nonyl group, decyl group, undecyl group, dodecyl group, tridecyl group, tetradecyl group, pentadecyl group, hexadecyl group, heptadecyl group, octadecyl group, nonadecyl group, isosyl group, or heneicosyl group; and $X^-$ is an anion of a pharmaceutically acceptable acid selected from the group consisting of chloride, acetate, citrate, nicotinate, nitrate, sulfonate and salicylate.

20. The method according to claim 18, wherein:

each of $R^1$ to $R^3$ is a methyl group, $R^4$ is a propionyl group, isobutyryl group, valeryl group, hexanoyl group, 4-methylvaleryl group, heptanoyl group, 2-propylvaleryl group, nonanoyl group, undecanoyl group, 10-undecenoyl group, tridecanoyl group, tetradecanoyl group, pentadecanoyl group, hexadecanoyl group, heptadecanoyl group, or linoleoyl group; and $R^5$ is propyl group, pentyl group, 2-methylbutyl group, isohexyl group, heptyl group, nonyl group, decyl group, undecyl group, dodecyl group, tridecyl group, tetradecyl group, pentadecyl group, heneicosyl group or 10-undecenyl group.

* * * * *